US008278348B2

(12) United States Patent
Boyd et al.

(10) Patent No.: US 8,278,348 B2
(45) Date of Patent: Oct. 2, 2012

(54) CHONDROPSIN-CLASS ANTITUMOR V-ATPASE INHIBITOR COMPOUNDS, COMPOSITIONS AND METHODS OF USE THEREOF

(75) Inventors: Michael R. Boyd, Mobile, AL (US); Kirk R. Gustafson, Frederick, MD (US)

(73) Assignee: The United States of America, as represented by the Secretary of the Department of Health and Human Services, Washington, DC (US)

( * ) Notice: Subject to any disclaimer, the term of this patent is extended or adjusted under 35 U.S.C. 154(b) by 54 days.

(21) Appl. No.: 12/909,979

(22) Filed: Oct. 22, 2010

(65) Prior Publication Data

US 2011/0034547 A1 Feb. 10, 2011

Related U.S. Application Data

(60) Continuation of application No. 12/402,560, filed on Mar. 12, 2009, now abandoned, which is a division of application No. 11/674,245, filed on Feb. 13, 2007, now Pat. No. 7,521,475, which is a division of application No. 10/521,930, filed as application No. PCT/US03/23290 on Jul. 24, 2003, now Pat. No. 7,205,334.

(60) Provisional application No. 60/398,092, filed on Jul. 24, 2002.

(51) Int. Cl.
| | |
|---|---|
| *A61K 31/35* | (2006.01) |
| *A61P 35/00* | (2006.01) |
| *A61P 35/02* | (2006.01) |
| *A61P 25/28* | (2006.01) |
| *A61P 19/10* | (2006.01) |
| *A61P 27/06* | (2006.01) |
| *A61P 15/08* | (2006.01) |
| *A61P 13/00* | (2006.01) |
| *A61P 31/10* | (2006.01) |
| *A61P 35/04* | (2006.01) |
| *A61P 19/08* | (2006.01) |

(52) U.S. Cl. ...................................... 514/450; 514/456
(58) Field of Classification Search .................. 514/450, 514/456
See application file for complete search history.

(56) References Cited

FOREIGN PATENT DOCUMENTS

| WO | WO 00/51589 | 9/2000 |
| WO | WO 02/08231 | 1/2002 |

OTHER PUBLICATIONS

Bowman et al., "Bafilomycins: A class of inhibitors of membrane ATPases from microorganisms, animal cells, and plant cells," *PNAS*, 85, 7972-7976 (1988).
Bowman et al., "Identification of a New Chondropsin Class of Antitumor Compound that Selectively Inhibits V-ATPases," *J. Biological Chemistry*, 278(45), 44147-44152 (2003).
Cantrell et al., "Chondropsins A and B: Novel Tumor Cell Growth-Inhibitory Macrolide Lactams from the Marine Sponge Chondropsis sp," *J. Am. Chem. Soc.*, 122, 8825-8829 (2000).
Dröse et al., "Bafilomycins and Concanamycins As Inhibitors of V-ATPases and P-ATPases," *J. Exp. Biol.*, 200, 1-8 (1997).
Dröse et al., "Inhibitory Effect of Modified Bafilomycins and Concanamycins on P- and V-Type Adenosinetriphosphatases," *Biochemistry*, 32, 3902-3906 (1993).
Rashid et al., "Chondropsin D, a New 37-Membered-Ring Macrolide Lactam from the Marine Sponge Chondropsis Species," *J. Nat. Prod.*, 64, 1341-1344 (2001).
Rashid et al., "Application of High-Field NMR and Cryogenic Probe Technologies in the Structural Elucidation of Poecillastrin A, a New Antitumor Macrolide Lactam from the Sponge Poecillastra Species," *Organic Lett.*, 4(19), 3293-3296 (2002).
Rashid et al., "New chondropsin macrolide lactams from marine sponges in the genus *Ircinia*," *Tetrahedron Lett.*, 42, 1623-1626 (2001).
PCT/US03/23290 International Search Report mailed Dec. 5, 2003.
Wang et al., "Oncogenesis Caused by Loss of the SNF5 Tumor Suppressor Is Dependent on Activity of BRG1, the ATPase of the SWI/SNF Chromatin remodeling Complex," *Cancer Research*, vol. 69, No. 20: 8094-8101 (2009).

*Primary Examiner* — Shengjun Wang
*Assistant Examiner* — Sahar Javanmard
(74) *Attorney, Agent, or Firm* — Leydig, Voit & Mayer

(57) ABSTRACT

A composition comprising a substantially purified compound of the formula:

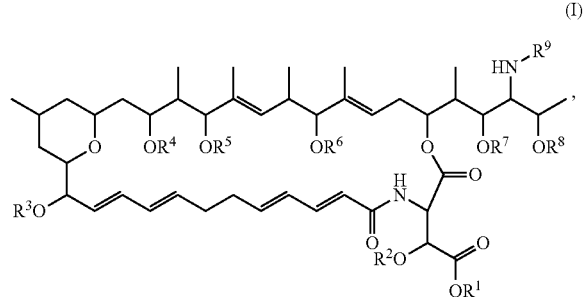

(I)

in combination with at least one additional therapeutic agent, and methods of preventing or treating cancer and a condition treatable by the inhibition of vacuolar-type (H+)-ATPase.

9 Claims, 3 Drawing Sheets

CHONDROPSIN-CLASS ANTITUMOR V-ATPASE INHIBITOR COMPOUNDS, COMPOSITIONS AND METHODS OF USE THEREOF

CROSS-REFERENCE TO RELATED APPLICATIONS

This patent application is a continuation of co-pending U.S. patent application Ser. No. 12/402,560, filed on Mar. 12, 2009, which is a divisional of U.S. patent application Ser. No. 11/674,245, filed on Feb. 13, 2007, now U.S. Pat. No. 7,521,475, which is a divisional of U.S. patent application Ser. No. 10/521,930, filed on Apr. 18, 2005, now U.S. Pat. No. 7,205,334, which is a U.S. national phase of International Patent Application No. PCT/US2003/023290, filed on Jul. 24, 2003, and which claims the benefit of U.S. Provisional Patent Application No. 60/398,092, which was filed on Jul. 24, 2002.

FIELD OF THE INVENTION

The present invention relates to vacuolar-type (H+)-ATPase-inhibiting macrocyclic lactams belonging to the chondropsin class of compounds, compositions, and methods of using them.

BACKGROUND OF THE INVENTION

Vacuolar (or vacuolar-type or V-type) (H+)-ATPases have been described as "a universal proton pump of eukaryotes" (Finbour and Harrison, *Biochem. J.*, 324, 697-712 (1997)). Vacuolar-type (H+)-ATPases are present in many tissues and cells of the body. Intracellular vacuolar (H+)-ATPase activities are present in certain organelles, and are responsible for maintaining the internal acidity thereof. This maintenance is essential for a variety of physiological functions such as: sorting of membrane and organellar proteins; proinsulin conversion; neurotransmitter uptake; cellular degradative processes; and, receptor cycling. See Mellman et al., *Ann. Rev. Biochem.*, 55, 663-699 (1986); Forgac, *Physiological Rev.*, 69, 765-796 (1989); Stevens and Forgac, *Annu. Rev. Cell. Dev. Biol.*, 13, 779-808 (1997); Nelson, TIPS, 12, 71-75 (1991).

Vacuolar-type (H+)-ATPase activity is also located within specialized plasma membranes. Important examples include the vacuolar-type (H+)-ATPase activity in the plasma membranes of kidney intercalated cells, osteoclasts and sperm cells. See Stone and Xie, *Kidney Int.*, 33, 767-774 (1988); Vaananen et al., *J. Cell. Biol.*, 111, 1305-1311 (1990); Blair et al., *Science*, 245, 855-857 (1987); Wang and Gluck, *J. Biol. Chem.*, 265, 21957-21965 (1990); Hall and Chambers, *Inflamm. Res.*, 45, 1-9 (1996); Hall and Schaueblin, *Bone and Mineral*, 27, 159-166 (1994); David and Baron, *Exp. Opin. Invest. Drugs*, 4, 725-740 (1995); Wassarman, *Science*, 235, 553-560 (1987); Nelson, TIPS, 12, 71-75 (1991).

Because of the importance of vacuolar-type (H+)-ATPase activity in the maintenance of many physiological functions, compounds which inhibit vacuolar-type (H+)-ATPase will have useful pharmacological applications in a variety of different situations. See reviews by Nelson, *TIPS*, 12, 71-74 (1991), and Keeling et al., *Ann. New York Acad. Sci.*, 834, 600-608 (1997), and references contained therein. For example, a given vacuolar-type (H+)-ATPase inhibitor may have utility against one or more disease states or physiological functions, in which it is desirable to inhibit an intra-organellar, vacuolar-type (H+)-ATPase-mediated process, such as acidification, accumulation of a neurotransmitter, receptor turnover, lysosomal storage, and the like. See Mellman et al., *Ann. Rev. Biochem.*, 55, 663-699 (1986); Forgac, *Physiological Rev.*, 69, 765-796 (1989); Stevens and Forgac, *Annu. Rev. Cell. Dev. Biol.*, 13, 779-808 (1997); Nelson, *TIPS*, 12, 71-75 (1991). Similarly, a given vacuolar-type (H+)-ATPase inhibitor may be useful against one or more disease states or physiological functions, in which it is desirable to modify a plasma membrane vacuolar-type (H+)-ATPase-mediated process, such as urinary acidification, bone resorption, or the acrosomal acid secretion required for fertility. See Stone and Xie, *Kidney Int.*, 33, 767-774 (1988); Vaananen et al, *J. Cell. Biol.*, 111, 1305-1311 (1990); Blair et al., *Science*, 245, 855-857 (1987); Wang and Gluck, *J. Biol. Chem.*, 265, 21957-21965 (1990); Hall and Chambers, *Inflamm. Res.*, 45, 1-9 (1996); Hall and Schaueblin, *Bone and Mineral*, 27, 159-166 (1994); David and Baron, *Exp. Opin. Invest. Drugs*, 4, 725-740 (1995); Wassarman, *Science*, 235, 553-560 (1987); Nelson, *TIPS*, 12, 71-75, (1991).

Compounds that inhibit vacuolar-type (H+)-ATPases also will have important utility for cancer therapy. For example, there is literature evidence indicating involvement of vacuolar-type (H+)-ATPases in processes related to cellular proliferation, angiogenesis, tumor cell invasiveness, metastasis, and drug resistance (see, e.g., Akifusa et. al., *Exp. Cell Res.*, 238, 82-89 (1998); Altan et al., *J. Exp. Med.*, 187, 1583-1598 (1998); Gerard et al., *J. Exp. Biol.*, 201, 21-31 (1998); Ishii et al., *J. Antibiot.*, 48, 12-20 (1995); Moriyama et al., *J. Biochem.*, 115, 213-218 (1994); Ohkuma et al., *In Vitro Cell Devel. Biol.*, 29A, 862-866 (1993); Perona et al., *Nature*, 334, 438-440 (1988); Montcourrier et al., *J. Cell Sci.*, 107, 2381-2391 (1994); Montcourrier et al., *Clin. Exp. Metastatis*, 15, 382-392 (1997); Martinez-Zaguilan et al., *Ann. NY Acad. Sci.*, 671, 478-480 (1992); Martinez-Zaguilan et al., *Am. J. Physiol.*, 265, C1015-C1029 (1993); Martinez-Zaguilan et al., *J. Cell. Physiol.*, 176, 196-205 (1998); Nishihara et al., *Biochem. Biophys. Res. Commun.*, 212, 255-262 (1995); Manabe et al., *J. Cell Physiol.*, 157, 445-452 (1993); Kinoshita et al., *FEBS Lett.*, 337, 221-225 (1994); Kinoshita et al., *FEBS Lett.*, 398, 61-66 (1996); Ohta et al., *Brit. J. Cancer*, 73, 1511-1517 (1996); Ohta et al., *J. Pathol.*, 185, 324-330 (1998); Marquardt et al., *J. Natl. Cancer Inst.*, 83, 1098-1102 (1991); and Banderra et al., *Int. J. Oncol.*, 12, 711-715 (1998)). Therefore, compounds that inhibit these phenomena will be useful in cancer chemotherapy.

Among the numerous challenges faced by medicinal chemistry research is the challenge of identifying new vacuolar-type (H+)-ATPase-inhibitory leads applicable to medical treatments. In addition, the identification and development of new leads useful in cancer chemotherapy remains a perplexing problem. Purely synthetic approaches toward the identification of novel anticancer agents and vacuolar-type (H+)-ATPase inhibiting agents have been typically unsuccessful, partly due to the technological and human limitations inherent in laboratory synthesis. Although biological metabolites provide a vast resource of new structurally diverse chemical compounds, the number of agents available for exploiting therapeutic opportunities are relatively few, particularly inhibitors of vacuolar-type (H+)-ATPase. For example, structural types that potently and selectively inhibit vacuolar-type (H+)-ATPases have thus far been limited to compounds such as bafilomycins, concanamycins, and benzolactone enamides such as the salicylihalamides and lobatamides (see Boyd, PCT International Patent Application No. PCT/US00/05582).

Thus, there remains a need for new vacuolar-type (H+)-ATPase inhibitors and anticancer compounds, pharmaceutical compositions, and methods of using them. The present invention provides such compounds, compositions, and methods. These and other advantages of the present invention, as well as additional inventive features, will be apparent from the description of the invention provided herein.

BRIEF SUMMARY OF THE INVENTION

The present invention provides a substantially purified compound of the formula:

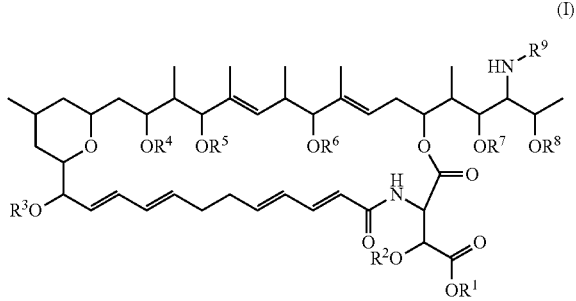

(I)

wherein:

$R^1$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof, wherein $R^1$ is unsubstituted or substituted with one or more substituents, which are the same or different, selected from the group consisting of a halogen, an oxo, $OR^{1a}$, $CO_2R^{1a}$, and $OC(O)R^{1a}$, wherein $R^{1a}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof;

$R^2$-$R^8$ are the same or different and each is $R^{10}$, $C(O)R^{10}$, $SO_3R^{10}$, or $SO_2R^{10}$, wherein $R^{10}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof, wherein $R^{10}$ is unsubstituted or substituted with one or more substituents, which are the same or different, selected from the group consisting of a halogen, an oxo, $OR^{10a}$, $CO_2R^{10a}$ and $OC(O)R^{10a}$, wherein $R^{10a}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof; and $R^9$ is a substituent of the formula:

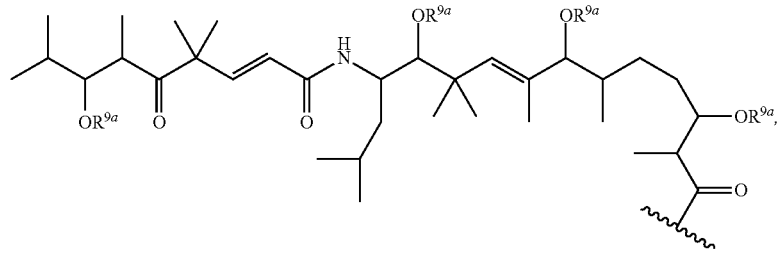

wherein the $R^{9a}$ substituents are the same or different and each is $R^{11}$, $C(O)R^{11}$, or $SO_2R^{11}$, wherein $R^{11}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof, wherein $R^{11}$ is unsubstituted or substituted with one or more substituents, which are the same or different, selected from the group consisting of a halogen, an oxo, $OR^{11a}$, $CO_2R^{11a}$ and $OC(O)R^{11a}$, wherein $R^{11a}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof;

wherein $R^{1a}$, $R^{10a}$ and $R^{11a}$ are unsubstituted or substituted with one or more substituents selected from the group consisting of a halogen, an oxo, and a hydroxyl. The compound of the present invention can be in the form of a pharmaceutically acceptable salt or a prodrug.

The present invention also provides a compound of the formula:

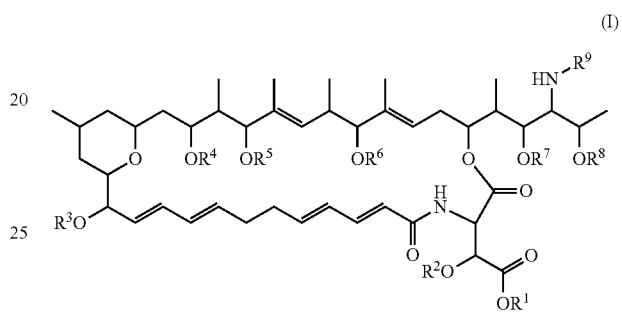

(I)

wherein:

$R^1$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof, wherein $R^1$ is unsubstituted or substituted with one or more substituents, which are the same or different, selected from the group consisting of a halogen, an oxo, $OR^{1a}$, $CO_2R^{1a}$, and $OC(O)R^{1a}$, wherein $R^{1a}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof;

$R^2$-$R^8$ are the same or different and each is $R^{10}$, $C(O)R^{10}$, $SO_3R^{10}$, or $SO_2R^{10}$, wherein $R^{10}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof, wherein $R^{10}$ is unsubstituted or substituted with one or more substituents, which are the same or different, selected from the group consisting of a halogen, an oxo, $OR^{10a}$, $CO_2R^{10a}$ and $OC(O)R^{10a}$, wherein $R^{10a}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof; and $R^9$ is a substituent of the formula:

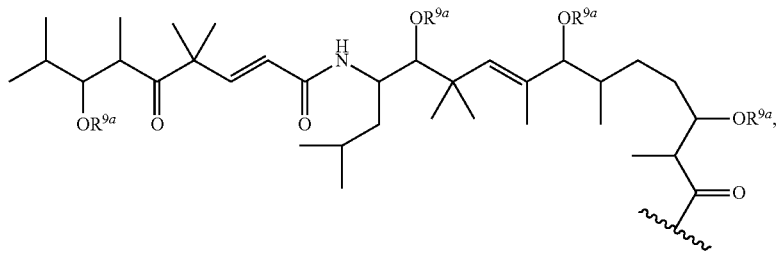

wherein the $R^{9a}$ substituents are the same or different and each is $R^{11}$, $C(O)R^{11}$, or $SO_2R^{11}$, wherein $R^{11}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof, wherein $R^{11}$ is unsubstituted or substituted with one or more substituents, which are the same or different, selected from the group consisting of a halogen, an oxo, $OR^{11a}$, $CO_2R^{11a}$ and $OC(O)R^{11a}$, wherein $R^{11a}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof;

wherein $R^{1a}$, $R^{10a}$ and $R^{11a}$ are unsubstituted or substituted with one or more substituents selected from the group consisting of a halogen, an oxo, and a hydroxyl;

or a pharmaceutically acceptable salt thereof, provided that the compound is not poecillastrin A.

The present invention additionally provides a composition comprising a therapeutically effective amount of at least one compound of the present invention, alone or in combination with at least one additional therapeutic agent. The therapeutically effect amount can be a vacuolar-type (H+)-ATPase-inhibiting effective amount and/or an anticancer effective amount.

The present invention further provides a method of preventing or treating a patient for a condition treatable by the inhibition of vacuolar-type (H+)-ATPase, said method comprises administering to the patient a vacuolar-type (H+)-ATPase-inhibiting effective amount of at least one compound of the present invention, whereupon the patient is treated for the condition.

The present invention also further provides a method of preventing or treating a patient for cancer, which method comprises administering to the patient an anticancer effective amount of at least one compound of the present invention, whereupon the patient is treated for cancer.

The compound(s) used in accordance with the present invention can be administered alone or in combination with a therapeutically effective amount of at least one additional therapeutic agent other than a compound of the present invention. Additional therapeutic agents include, for example, vacuolar-type (H+)-ATPase inhibitors and anticancer compounds.

DETAILED DESCRIPTION OF THE INVENTION

Figure 1A:
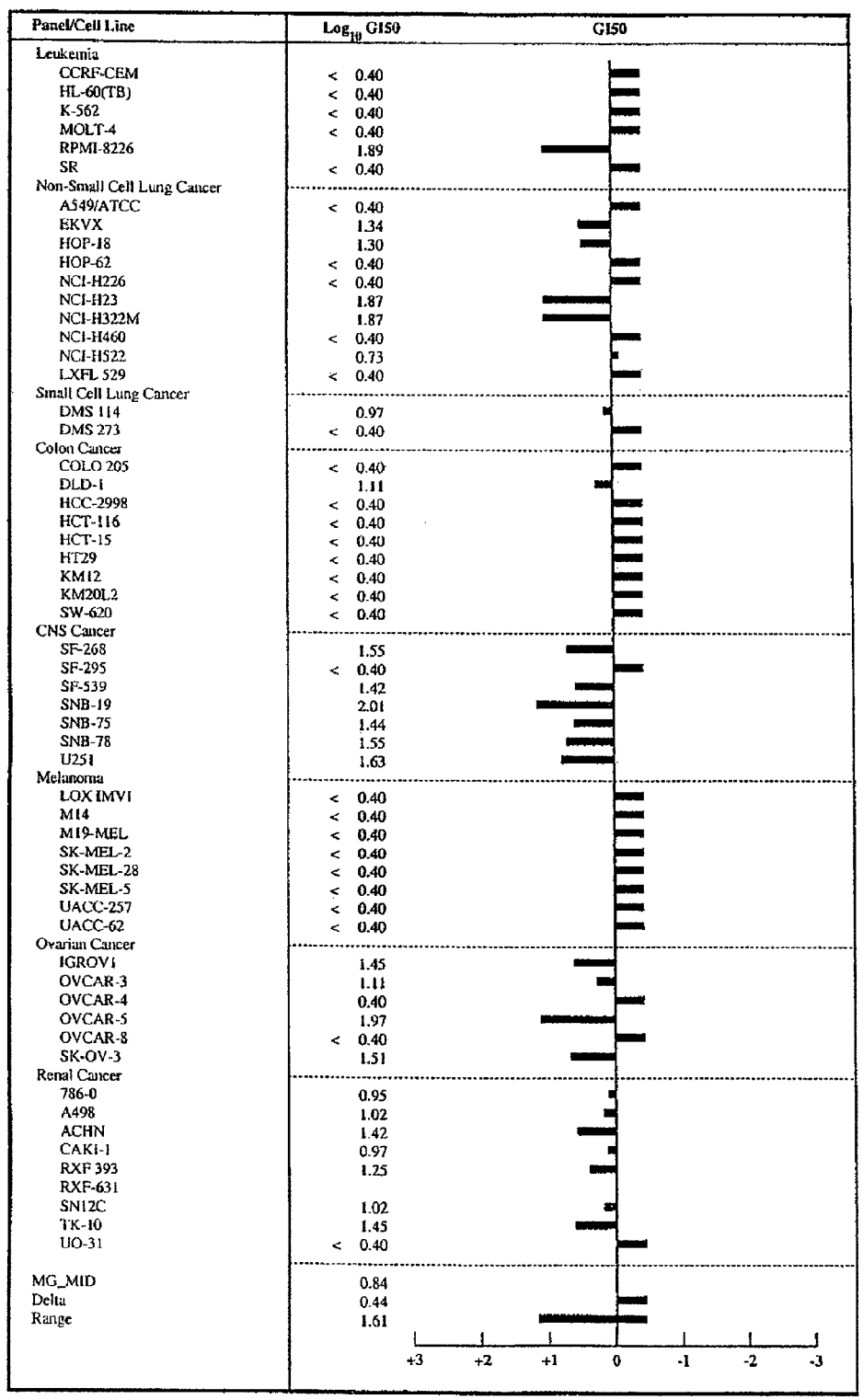
FIG. 1A illustrates the $GI_{50}$-based mean-graph "fingerprint" of an extract of Poecillastra species in the NCI 60 cell-line screen.

The present invention provides a substantially purified compound of the formula:

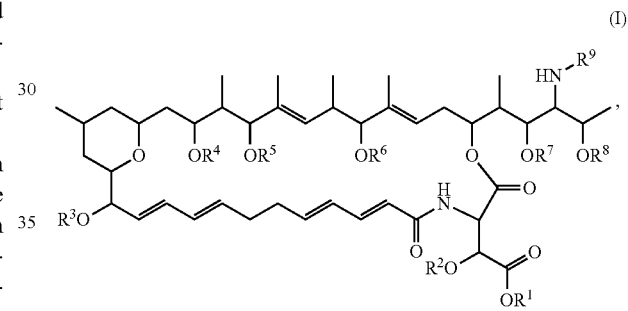

wherein:

$R^1$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof, wherein $R^1$ is unsubstituted or substituted with one or more substituents, which are the same or different, selected from the group consisting of a halogen, an oxo, $OR^{1a}$, $CO_2R^{1a}$, and $OC(O)R^{1a}$, wherein $R^{1a}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof;

$R^2$-$R^8$ are the same or different and each is $R^{10}$, $C(O)R^{10}$, $SO_3R^{10}$, or $SO_2R^{10}$, wherein $R^{10}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof, wherein $R^{10}$ is unsubstituted or substituted with one or more substituents, which are the same or different, selected from the group consisting of a halogen, an oxo, $OR^{10a}$, $CO_2R^{10a}$ and $OC(O)R^{10a}$, wherein $R^{10a}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof; and $R^9$ is a substituent of the formula:

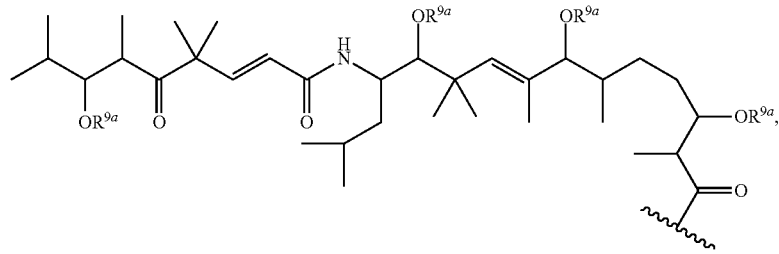

wherein the $R^{9a}$ substituents are the same or different and each is $R^{11}$, $C(O)R^{11}$, or $SO_2R^{11}$, wherein $R^{11}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof, wherein $R^{11}$ is unsubstituted or substituted with one or more substituents, which are the same or different, selected from the group consisting of a halogen, an oxo, $OR^{11a}$, $CO_2R^{11a}$ and $OC(O)R^{11a}$, wherein $R^{11a}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof;

wherein $R^{1a}$, $R^{10a}$ and $R^{11a}$ are unsubstituted or substituted with one or more substituents selected from the group consisting of a halogen, an oxo, and a hydroxyl. The compound of the present invention can be in the form of a pharmaceutically acceptable salt or a prodrug.

Preferred substituents for $R^1$-$R^8$ include H and a straight-chain or branched $C_{1-30}$ saturated alkyl. Substituent $R^3$ is preferably hydrogen or methyl. Preferred $R^{9a}$ substituents include H and a straight-chain or branched $C_{1-30}$ saturated alkyl. More preferably $R^{9a}$ is H.

In a preferred embodiment, $R^3$ is methyl and $R^1$, $R^2$, $R^4$-$R^8$ and $R^{9a}$ are H.

Another embodiment of the invention includes a compound of the formula:

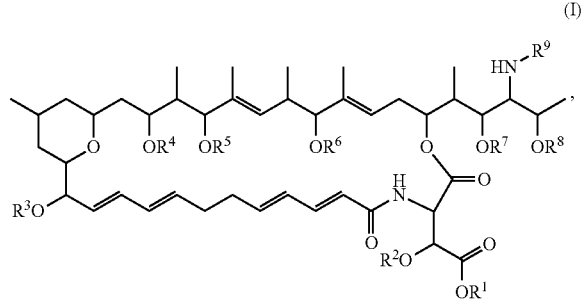

(I)

wherein:

$R^1$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof, wherein $R^1$ is unsubstituted or substituted with one or more substituents, which are the same or different, selected from the group consisting of a halogen, an oxo, $OR^{1a}$, $CO_2R^{1a}$, and $OC(O)R^{1a}$, wherein $R^{1a}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof;

$R^2$-$R^8$ are the same or different and each is $R^{10}$, $C(O)R^{10}$, $SO_3R^{10}$, or $SO_2R^{10}$, wherein $R^{10}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof, wherein $R^{10}$ is unsubstituted or substituted with one or more substituents, which are the same or different, selected from the group consisting of a halogen, an oxo, $OR^{10a}$, $CO_2R^{10a}$ and $OC(O)R^{10a}$, wherein $R^{10a}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof; and $R^9$ is a substituent of the formula:

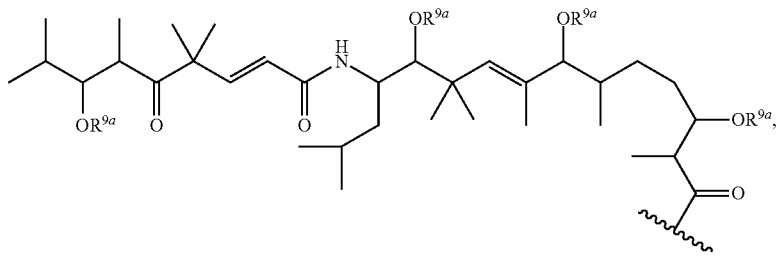

wherein the $R^{9a}$ substituents are the same or different and each is $R^{11}$, $C(O)R^{11}$, or $SO_2R^{11}$, wherein $R^{11}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof, wherein $R^{11}$ is unsubstituted or substituted with one or more substituents, which are the same or different, selected from the group consisting of a halogen, an oxo, $OR^{11a}$, $CO_2R^{11a}$ and $OC(O)R^{11a}$, wherein $R^{11a}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof;

wherein $R^{1a}$, $R^{10a}$ and $R^{11a}$ are unsubstituted or substituted with one or more substituents selected from the group consisting of a halogen, an oxo, and a hydroxyl;

or a pharmaceutically acceptable salt thereof, provided that the compound is not poecillastrin A.

In a particularly preferred embodiment, the present invention includes a substantially purified compound of the formula:

The term "saturated alkyl" means a straight-chain or branched-chain saturated alkyl which can contain from about 1 to about 30 carbon atoms, for example, from about 1 to about 20 carbon atoms, from 1 to about 10 carbon atoms, from about 1 to about 8 carbon atoms, or from about 1 to about 6 carbon atoms. Examples of saturated alkyls include methyl, ethyl, propyl, isopropyl, n-butyl, sec-butyl, isobutyl, tert-butyl, pentyl, isoamyl, hexyl, octyl, dodecanyl, octadecyl, and the like. Saturated alkyl substituents can be unsubstituted or substituted, for example, with at least one substituent selected from the group consisting of a halogen, a nitro, an amino, a hydroxyl, a thio, an acyl, an alkyl, and a cyano.

The term "unsaturated alkyl" means saturated alkyl (straight-chain or branched-chain), as defined herein, in which one or more of the single carbon-carbon bonds thereof is instead a multiple bond, for example, a double or a triple bond. Thus, unsaturated alkyls include alkenyl and alkynyl substituents, as well as substituents that have a combination of double and triple bonds. The term "alkenyl" means a

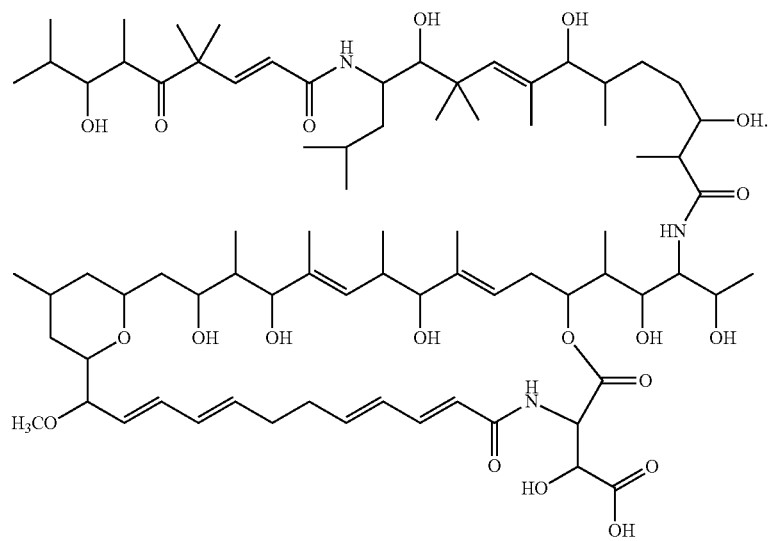

Another particularly preferred embodiment includes a substantially purified compound of the formula:

straight-chain or branched-chain alkenyl having one or more double bonds. Unless otherwise specified, the alkenyl can

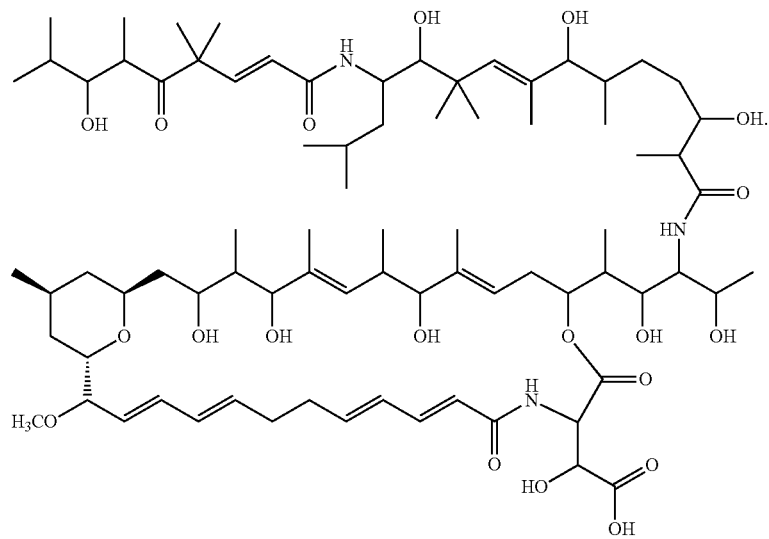

contain from about 2 to about 30 carbon atoms, for example, from about 2 to about 20 carbon atoms, from about 2 to about 10 carbon atoms, from about 2 to about 8 carbon atoms, or from about 2 to about 6 carbon atoms. Examples of alkenyls include vinyl, allyl, 1,4-butadienyl, isopropenyl, and the like. The term "alkynyl" means a straight-chain or branched-chain alkynyl radical having one or more triple bonds. Unless otherwise specified, alkynyls can contain from about 2 to about 30 carbon atoms, for example, from about 2 to about 20 carbon atoms, from about 2 to about 10 carbon atoms, from about 2 to about 8 carbon atoms, or from about 2 to about 6 carbon atoms. Examples of alkynyls include ethynyl, propynyl (propargyl), butynyl, and the like. Unsaturated alkyl substituents can be unsubstituted or substituted, for example, with at least one substituent selected from the group consisting of a halogen, a nitro, an amino, a hydroxyl, a thio, an acyl, an alkyl, and a cyano.

The term "aryl" means an aromatic carbocyclic radical, as commonly understood in the art, and includes monocyclic and polycyclic aromatics such as, for example, phenyl and naphthyl rings. Preferably, the aryl comprises one or more six-membered rings including, for example, phenyl, naphthyl, biphenyl and the like. More preferably, the aryl comprises about six to about ten carbons. Aryl substituents can be unsubstituted or substituted, for example, with at least one substituent selected from the group consisting of a halogen, a nitro, an amino, a hydroxyl, a thio, an acyl, an alkyl, and a cyano.

It will be appreciated that the compounds of the present invention can be obtained by methods known to those of skill in the art, for example, by structurally modifying poecillastrin A, or by direct synthesis, using routine synthetic transformations that are well known in the art. One or more hydroxyl groups, for example, can be converted to the oxo derivative by direct oxidation. Direct oxidation can be accomplished using any known method such as, for example, a Swern oxidation, or by reaction with a metal oxidant such as a chromium oxide (e.g., chromium trioxide), a manganese oxide (e.g., manganese dioxide or permanganate) or the like. Primary alcohols can be oxidized to aldehydes, for example, via Swern oxidation, or they can be oxidized to carboxylic acids (e.g., $CO_2H$), for example, by reaction with a metal oxidant as described herein. Similarly, thiols (e.g., SR, SH or the like) can be converted to oxidized sulfur derivatives (e.g., $SO_2R$, $SO_3H$, or the like) by reaction with an appropriate oxidant.

One or more hydroxyl groups also can be converted to an ester (e.g., $CO_2R$) by reaction with an appropriate esterifying agent such as, for example, an anhydride (e.g., $(R(CO))_2O$) or an acid chloride (e.g., R(CO)Cl), or the like, or converted to a sulfonate (e.g., $SO_2R$) by reaction with an appropriate sulfonating agent such as, for example, a sulfonyl chloride (e.g., $RSO_2Cl$), or the like, wherein R is any suitable substituent including, for example, organic substituents described herein. Carboxylate esters also can be obtained by reacting one or more carboxylic acids (e.g., $CO_2H$) with an alkylating agent such as, for example, a diazoalkane (e.g., diazomethane), an alkyl or aryl iodide, or the like. One or more amides can be obtained by reaction of one or more carboxylic acids with an amine under appropriate amide-forming conditions. Appropriate amide-forming conditions include, for example, activation of a carboxylic acid (e.g., by conversion to an acid chloride or by reaction with a carbodiimide reagent) followed by coupling of the activated species with a suitable amine.

One or more hydroxyl groups also can be converted to a halogen atom using a halogenating agent such as, for example, an N-halosuccinimide such as N-iodosuccinimide, N-bromosuccinimide, N-chlorosuccinimide or the like, in the presence of a suitable activating agent (e.g., a phosphine or the like). One or more hydroxyl groups also can be converted to an ether by reacting one or more hydroxyls, for example, with an alkylating agent in the presence of a suitable base. Suitable alkylating agents can include, for example, an alkyl or aryl sulfonate, an alkyl or aryl halide, or the like. One or more suitably activated hydroxyls, for example, a sulfonate ester, and/or one or more suitably active halides, can be converted to the corresponding thiol, cyano, halo, or amino derivative by displacement with a nucleophile. Suitable nucleophiles can include, for example, a thiol, a cyano, a halide ion, an amine (e.g., $NH_2R^9$, wherein $R^9$ is as described herein), or the like.

Functional groups such as, for example, amines can be obtained by a variety of methods known in the art. Amines can be obtained by hydrolysis of one or more amides such as, for example, one or more of the amides in poecillastrin A. Amines also can be obtained by reacting one or more suitable oxo groups (e.g., an aldehyde or a ketone) with one or more suitable amines under the appropriate conditions, for example, reductive amination conditions, or the like. One or more amines, in turn, can be converted to a number of other useful derivatives such as, for example, amides, sulfonamides and the like.

Other structural modifications can be accomplished by incorporating synthetic, semisynthetic or naturally occurring materials such as, for example, one or more amino acids, into the structure of one or more compounds of formula (I). For example, modifications of $R^1$ and/or $R^8$ can be accomplished by incorporating different amino acids into the macrocyclic ring skeleton of formula (I). Such amino acids can include, for example, aspartic acid, phenyl alanine, serine, leucine, analogs thereof, homologs thereof, and the like. It will be appreciated that a number of other synthetic transformations can be accomplished, other than those described herein, using routine chemistry that is well known in the art. As such, the transformations and structural modifications described herein are in no way limiting, but are only illustrative for preparing various compounds of the present invention.

Surprisingly and unexpectedly it has been found that compounds of formula (I) have anticancer activity and, further surprisingly, vacuolar-type (H+)-ATPase inhibitory activity. The compounds of the present invention can be obtained by one of ordinary skill in the art by isolation from natural sources; chemical synthesis using well-known and readily available chemical reactions, reagents, and procedures; by semisynthesis; or the like. The structure of formula (I) furthermore provides a practical template that can be used to produce a vast number of structurally diverse, yet synthetically accessible, vacuolar-type (H+)-ATPase inhibitors and anticancer compounds.

One or more compounds of the present invention can be included in a composition, e.g., a pharmaceutical composition. In that respect, the present invention further provides a composition that includes a therapeutically effective amount of at least one compound of the present invention and a pharmaceutically acceptable carrier. The therapeutically effective amount can include an amount that produces a therapeutic or prophylactic response in a patient to whom a compound or composition of the present invention is administered. A therapeutically effective amount can include, for example, a vacuolar-type (H+)-ATPase-inhibiting effective amount and/or an anticancer effective amount.

The composition of the present invention can further include a therapeutically effective amount of at least one additional compound other than a compound of the present invention, for example, a compound other than a compound of formula (I). When an additional compound is included in the composition of the present invention, the additional compound can be a vacuolar-type (H+)-ATPase-inhibiting compound (e.g., a concanamycin or a bafilomycin or a benzolactone enamide, such as a salicylihalamide or a lobatamide). One or more additional anticancer compounds, other than a compound of the present invention, also can be included. When the additional compound is a vacuolar-type (H+)-ATPase-inhibitor other than a compound of the present invention, it is preferably present in the composition in a vacuolar-type (H+)-ATPase-inhibiting effective amount. When the additional compound is an anticancer compound, it is preferably present in the composition of the present invention in an anticancer effective amount.

The composition of the present invention can be produced by combining one or more compounds of the present invention with an appropriate pharmaceutically acceptable carrier, and can be formulated into a suitable preparation. Suitable preparations include, for example, preparations in solid, semi-solid, liquid, or gaseous forms such as tablets, capsules, powders, granules, ointments, solutions, suppositories, injections, inhalants, and aerosols, and other formulations known in the art for their respective routes of administration. In pharmaceutical dosage forms, a compound of the present invention can be used alone or in appropriate association, as well as in combination, with other pharmaceutically active compounds, including other vacuolar-type (H+)-ATPase inhibiting compounds, as described herein.

Any suitable carrier can be utilized. Suitable carriers include pharmaceutically or physiologically acceptable carriers. The following methods and carriers are merely exemplary and are in no way limiting. In the case of oral preparations, a compound of the present invention can be administered alone or in combination with a therapeutically effective amount of at least one other compound. The active ingredient(s) can be combined, if desired, with appropriate additives to make tablets, powders, granules, capsules, or the like.

Suitable additives can include, for example, lactose, mannitol, corn starch or potato starch. Suitable additives also can include binders, for example, crystalline cellulose, cellulose derivatives, acacia, corn starch, or gelatins; disintegrants, for example, corn starch, potato starch or sodium carboxymethylcellulose; with lubricants such as talc or magnesium stearate. If desired, other additives such as, for example, diluents, buffering agents, moistening agents, preservatives, and/or flavoring agents, and the like, can be included in the composition.

The compounds used in accordance with the present invention can be formulated into a preparation for injection by dissolution, suspension, or emulsification in an aqueous or nonaqueous solvent, such as vegetable oil, synthetic aliphatic acid glycerides, esters of higher aliphatic acids, or propylene glycol (if desired, with conventional additives such as solubilizers, isotonic agents, suspending agents, emulsifying agents, stabilizers, and preservatives). The compounds of the present invention also can be made into an aerosol formulation to be administered via inhalation. Such aerosol formulations can be placed into pressurized acceptable propellants such as dichlorodifluoromethane, fluorohydrocarbons, propane, nitrogen, and the like.

The compounds of the present invention can be formulated into suppositories by admixture with a variety of bases such as emulsifying bases or water-soluble bases. The suppository formulations can be administered rectally, and can include vehicles such as cocoa butter, carbowaxes, and polyethylene glycols, which melt at body temperature, but are solid at room temperature.

Unit dosage forms for oral or rectal administration such as syrups, elixirs, and suspensions can be provided wherein each dosage unit, e.g., teaspoonful, tablespoonful, tablet, or suppository contains a predetermined amount of the composition containing the compound of the present invention. Similarly, unit dosage forms for injection or intravenous administration can comprise a composition as a solution in sterile water, normal saline, or other pharmaceutically acceptably carrier.

The term "unit dosage form" as used herein refers to physically discrete units suitable as unitary dosages for human and animal subjects, each unit containing a predetermined quantity of at least one compound or compounds of the present invention (alone or, if desired, in combination with another therapeutic agent). The unit dosage can be determined by methods known to those of skill in the art, for example, by calculating the amount of active ingredient sufficient to produce the desired effect in association with a pharmaceutically acceptable carrier. The specifications for the unit dosage forms that can be used in accordance with the present invention depend on the particular effect to be achieved and the particular pharmacodynamics associated with the compound(s) in the individual host.

Pharmaceutically acceptable carriers, for example, vehicles, adjuvants, excipients, or diluents, are accessible to those of skill in the art and are typically available commercially. One skilled in the art can easily determine the appropriate method of administration for the exact formulation of the composition being used. Any necessary adjustments in dose can be readily made by a skilled practitioner to address the nature or severity of the condition being treated. Adjustments in dose also can be made on the basis of other factors such as, for example, the individual patient's overall physical health, sex, age, prior medical history, and the like.

The dose administered to a mammal, particularly a human, in the context of the present invention should be sufficient to effect a therapeutic response in the mammal over a reasonable time frame. The dose will be determined by the strength of the particular composition employed (taking into consideration, at least, the bioactivity of any decomposition products derived from the compounds) and the condition of the mammal (e.g., human), as well as the body weight of the mammal (e.g., human) to be treated. The size of the dose also will be determined by the existence, nature, and extent of any adverse side effects that might accompany the administration of a particular composition. A suitable dosage for internal administration is 0.01 to 100 mg/kg of body weight per day, such as 0.01 to 35 mg/kg of body weight per day or 0.05 to 5 mg/kg of body weight per day. A suitable concentration of the conjugate in pharmaceutical compositions for topical administration is 0.05 to 15% (by weight), preferably 0.02 to 5%, and more preferably 0.1 to 3%.

The compounds of the present invention can be utilized in a variety of therapeutic and non-therapeutic applications. It will be appreciated that one or more compounds of the present invention can be used, for example, as a control in diagnostic kits, bioassays, or the like. Preferably, the method of the present invention is applied therapeutically, for example, toward the treatment or prevention of cancer or toward the treatment or prevention a condition (e.g., an abnormal condition or a disease) treatable by the inhibition of vacuolar-type (H+)-ATPase. The compound(s) of the present invention can be administered alone, or in combination with a therapeutically effective amount of at least one additional compound other than a compound of the present invention.

Accordingly, the present invention further provides a method of treating or preventing a condition treatable by the inhibition of vacuolar-type (H+)-ATPase, which method includes administering to a patient a vacuolar-type (H+)-ATPase-inhibiting amount of at least one compound of the present invention. More particularly, the present invention provides a method of treating or preventing a condition treatable by the inhibition of vacuolar-type (H+)-ATPase, which method includes administering a vacuolar-type (H+)-ATPase inhibiting-effective amount of at least one compound of formula (I). By "prophylactic" is meant any degree in inhibition of vacuolar-type (H+)-ATPase or inhibition of the onset of cancer, including complete inhibition. By "therapeutic" is meant any degree in inhibition of vacuolar-type (H+)-ATPase or inhibition of the growth or metastasis of the cancer in the mammal (e.g., human).

A number of conditions can be treated in accordance with the method of the present invention. The vacuolar-type (H+)-ATPase inhibiting compounds and compositions of the present invention can be used medically to regulate biological phenomena including, but not limited to: intra-organellar acidification of intracellular organelles; urinary acidification; bone resorption; fertility; angiogenesis; cellular invasiveness (e.g., tumor cell invasiveness); tumor cell proliferation and metastasis; and the development of drug resistance in tumor cells. The compounds of the present invention are therefore useful in the treatment of diseases that can be controlled by the inhibition of vacuolar-type (H+)-ATPase. Such diseases include, for example, osteoporosis (see, e.g., Keeling et al., *Ann. New York Acad. Sci.*, 834, 600-608 (1997)), Alzheimer's disease, glaucoma, and abnormal urinary acidification (see, e.g., Nelson, *TIPS*, 12, 71-75 (1991)). Moreover, the vacuolar-type (H+)-ATPase inhibitors of the present invention can be used in the treatment or prevention of diseases which utilize an acid-promoted cell penetration mechanism. For example, the compounds of the present invention can be used to inhibit the entry of viruses (e.g., baculoviruses and retroviruses), or to inhibit the entry of protein toxins (e.g., diphtheria toxin), into cells (see, e.g., Mellman et al., *Ann. Rev. Biochem.*, 55, 663-699 (1986)). The compounds of the present invention also can be used to inhibit fertility in an animal, for example, a human (see, e.g., Wassarman, *Science*, 235, 553-560 (1987)), or to inhibit the proliferation, invasiveness or metastasis of tumor cells, or to promote the sensitivity of cancer toward drugs by inhibiting the ability of cancer cells to develop resistance to drugs, thereby facilitating and/or making possible the chemotherapeutic treatment of cancer (see, e.g., Marquardt and Center, *J. Natl. Cancer Inst.*, 83, 1098-1102 (1991)).

Thus, as indicated above, the method of the present invention include a method of treating conditions selected from the group consisting of osteoporosis, Alzheimer's disease, glaucoma, fertility, abnormal urinary acidification, abnormal secretion of degradative enzymes, and cancer. In accordance with method of the present invention, it is preferred that a vacuolar-type (H+)-ATPase inhibiting-effective amount is used. In that regard, it is preferred that the vacuolar-type (H+)-ATPase inhibiting-effective amount is effective to inhibit one or more conditions selected from the group consisting of intra-organellar acidification of intracellular organelles, urinary acidification, bone resorption, fertility, drug-resistance of tumor cells, tumor cell proliferation, cellular invasiveness, angiogenesis, and metastasis.

The method of the present invention further includes administering a vacuolar-type (H+)-ATPase inhibiting-effective amount of at lease one additional compound other than a compound of the present invention, e.g., a compound other than a compound of formula (I). In some instances, the method of the present invention can be made more effective by administering one or more other vacuolar-type (H+)-ATPase inhibitors (e.g., a concanamycin and/or a bafilomycin and/or benzolactone enamide, such as a salicylihalamide or a lobatamide), along with a compound of the present invention. One or more compounds of the present invention also can be co-administered in combination with an anticancer agent other than a compound of the present invention, for example, to inhibit the development of cancer cell resistance to the anticancer agent.

In accordance with the method of the present invention, one or more compounds of the present invention can be administered by any suitable route including, for example, oral administration, intramuscular administration, subcutaneous, intravenous administration, or the like. For example, one or more vacuolar-type (H+)-ATPase inhibitors of the present invention (or a composition thereof) can be administered as a solution that is suitable for intravenous injection or infusion, a tablet, a capsule, or the like, or in any other suitable composition or formulation as described herein.

The vacuolar-type (H+)-ATPase "inhibiting-effective amount," as utilized in accordance with the composition and method of the present invention, includes the dose necessary to achieve a vacuolar-type (H+)-ATPase "inhibiting-effective level" of the active compound in an individual patient. The vacuolar-type (H+)-ATPase inhibiting-effective amount can be defined, for example, as that amount required to be administered to an individual patient to achieve a vacuolar-type (H+)-ATPase inhibiting-effective blood level, tissue level, and/or intracellular level of a compound of the present invention to effect the desired medical treatment.

When the effective level is used as the preferred endpoint for dosing, the actual dose and schedule can vary depending, for example, upon interindividual differences in pharmacokinetics, drug distribution, metabolism, and the like. The effective level also can vary when one or more compounds of the present invention are used in combination with other therapeutic agents, for example, one or more additional vacuolar-type (H+)-ATPase inhibitors, anticancer compounds, or a combination thereof. Moreover, the effective level can vary depending upon the disease for which treatment is desired. For example, the effective level for the treatment of osteoporosis may vary relative to the effective level required for the treatment of abnormal urinary acidification, or for the inhibition of fertility.

The unique vacuolar-type (H+)-ATPase inhibitory activity of the compounds of the present invention can be determined using any suitable method known in the art, for example, assay methods. A suitable assay method for measuring vacuolar-type (H+)-ATPase inhibitory activity is described, for example, in Chan et al., *Anal. Biochem.*, 157, 375-380 (1986). Alternatively, the unique vacuolar-type (H+)-ATPase inhibitory activity of the compounds of the present invention can be demonstrated using the U.S. National Cancer Institute's (NCI)'s 60 cell-line, human tumor, disease-oriented screen, which can accurately predict the anticancer activity of chemical compounds. Significantly, the NCI 60 cell-line screen also is a powerful tool that can be used to predict other types of biological activity, not limited to anticancer activity. In particular, the NCI 60 cell-line screen can be used to accurately predict antitumor activity as well as vacuolar-type (H+)-ATPase inhibitory activity (see Boyd, PCT International Patent Application No. PCT/US00/05582).

Irrespective of vacuolar-type (H+)-ATPase inhibitory activity, the compounds of the present invention have anticancer activity against a number of different cancer cell lines, including human cancers, as demonstrated in the NCI 60 cell-line screen. Exemplary compounds of the present invention possess potent antitumor activity (see, e.g., Example 3). To the extent that the compounds used in accordance with the present invention have anticancer activity, the effective blood level can be determined by analogy based on the effective blood level corresponding to anticancer activity. As indicated above, the NCI 60 cell-line human tumor screen measures the ability of a compound to selectively kill or inhibit the growth of diverse human cancers. Using this screen, it is shown that the compounds of the present invention are highly active against certain types of human solid tumors (e.g., non-small cell lung cancer, renal cancer, and melanoma), which are very resistant or completely resistant to existing anticancer drugs. It is also shown that the compounds of the present invention are active against many other types of human solid tumors and leukemia cancer cells. By these observations, and with other detailed analyses of tumor cellular response profiles, it can be demonstrated that the compounds of the present invention are novel anticancer agents having considerable promise, for example, as therapeutic agents for the treatment of human solid tumors.

The compounds of the present invention are thus new and broadly efficacious anticancer agents, which inhibit or destroy human leukemias, lymphomas, melanomas and solid tumors. Solid tumors may include lung cancer (e.g., non-small cell lung cancer), colon cancer, CNS cancer (e.g., brain cancer), melanoma, ovarian cancer, renal cancer, prostate cancer, head and neck cancer, testicular cancer, germ-line cancers, endocrine tumors, uterine cancer, breast cancer, sarcomas, gastric cancer, hepatic cancer, esophageal cancer, pancreatic cancer, and the like. Preferably the cancer is colon cancer, melanoma, breast cancer, ovarian cancer or non-small lung cancer.

The need for new classes of anticancer drugs remains an urgent worldwide priority, which is being addressed effectively through new research and development applications of the NCI 60 cell-line screen. Reviews can be found, for example, in Boyd and Paull, *Drug Dev. Res.*, 34, 91-109 (1995); Weinstein et al., *Science*, 275, 343-349 (1997); and Greyer and Chabner, In: *Cancer: Principles and Practice of Oncology*, 5th Ed. (DeVita, V. T., et al., eds.), Philadelphia: Lippincott-Raven, 1977, pp. 385-394. The NCI screen provides an unprecedentedly rich information content to support the identification of important new classes of anticancer drugs. For example, see Weinstein et al., *Science*, 275, 343-349 (1997); Greyer and Chabner, In: *Cancer: Principles and Practice of Oncology*, 5th Ed. (DeVita, V. T., et al., eds.), Philadelphia: Lippincott-Raven, 1977, pp. 385-394; and Sausville, In: *Anticancer Drug Development Guide: Preclinical Screening, Clinical Trials, and Approval* (Teicher, B. A., ed.), Totowa, N.J.: Humana Press, Inc., 1997, pp. 217-226.

Accordingly, the present invention further provides a method of preventing or treating cancer, which method comprises administering an anticancer effective amount of at least one compound of the present invention. The anticancer effective amount can be determined by methods known in the art including, for example, by determining an amount to be administered effective to produce an "effective level" in the subject patient. The effective level can be chosen, for example, as that level (e.g., $10^{-11}$–$10^{-7}$ M) effective to inhibit the proliferation of tumor cells in a screening assay. Similarly, the effective level can be determined, for example, on the basis of the blood or tissue level in a patient that corresponds to a concentration of a therapeutic agent that effectively inhibits the growth of human cancers in an assay that is clinically predictive of anticancer activity. Further, the effective level can be determined, for example, based on a concentration at which certain markers of cancer in a patient's blood are inhibited by a particular compound that inhibits cancer. Alternatively, the effective level can be determined, for example, based on a concentration effective to slow or stop the growth of a patient's cancer, cause a patient's cancer to regress or disappear, render a patient asymptomatic to a particular cancer, or improve a cancer patient's subjective sense of condition. The anticancer effective level can then be used to approximate (e.g., by extrapolation), or even to determine, the level, which is required clinically to achieve a vacuolar-type (H+)-ATPase inhibiting-effective blood, tissue, and/or intracellular level to effect the desired medical treatment. It will be appreciated that the determination of the therapeutically effective amount clinically required to effectively inhibit vacuolar-type (H+)-ATPase activity requires consideration of other variables that can influence the effective level, as discussed herein. When a fixed effective amount is used as a preferred endpoint for dosing, the actual dose and dosing schedule for drug administration can vary for each patient depending upon factors that include, for example, inter-individual differences in pharmacokinetics, drug disposition, metabolism, whether other drugs are used in combination, or other factors described herein that effect the effective level.

One skilled in the art can readily determine the appropriate dose, schedule, or method of administering a particular formulation, in order to achieve the desired effective level in an individual patient. One skilled in the art also can readily determine and use an appropriate indicator of the effective level of the compounds of the present invention. For example, the effective level can be determined by direct analysis (e.g., analytical chemistry) or by indirect analysis (e.g., with clinical chemistry indicators) of appropriate patient samples (e.g., blood and/or tissues). The effective level also can be determined, for example, by direct or indirect observations such as urine acidity, change in bone density, decrease in ocular pressure, or by the shrinkage or inhibition of growth of a tumor in a cancer patient (e.g., if the compound in question has anticancer activity). There are many references in the art that describe the protocols used in administering active compounds to a patient in need thereof. For example, the protocols used in the administration of anticancer agents to patients are described in "Cancer Chemotherapy: Principles and Practice" ed., Chabner and Collins, J. B. Lippincott, 1990, especially chapter 2, by J. B. Collins. See also Boyd, WO 99/05136.

The present inventive method of preventing or treating cancer further includes administering an anticancer effective amount of at least one additional compound other than a compound of the present invention, for example, a compound other than a compound of formula (I). For example, one or more compounds of the present invention can be co-administered with an anticancer agent, in which case the effective level desirably is the level needed to inhibit the ability of the cancer to develop resistance to the anticancer agent. Suitable anticancer compounds include, for example, all of the known anticancer compounds approved for marketing in the United States, and those that will become approved in the future, for which drug resistance thereto can be controlled by the inhibition of vacuolar-type (H+)-ATPase.

The demonstration of antitumor, vacuolar-type (H+)-ATPase-inhibitory and other biological activities is based on the correlation of activity patterns generated in the NCI screen by compounds having known activity. The compounds compared in the correlation need not have particularly potent anticancer activity in order to display an activity pattern suitable for correlation in the NCI screen. Interestingly, compounds need not be structurally similar to one another in order correlate with each other in the NCI screen. Even if two structurally dissimilar compounds correlate strongly with each other in the NCI screen, they can be accurately predicted to have the same biological activity as each other in virtually any application, including non-cancer applications. For reviews pertinent to the NCI 60 cell-line screen, see Boyd, In: *Current Therapy in Oncology* (Niederhuber, ed.), Philadelphia: B. C. Decker, Inc., 1993, pp. 11-22; Boyd and Paull, *Drug Dev. Res.*, 34, 91-109 (1995); Greyer and Chabner, In: *Cancer Principles and Practice of Oncology*, 5th Ed. (DeVita et al., eds.), Philadelphia: Lippincott-Raven, 1977, pp. 385-394; Paull et al., In: *Cancer Chemotherapeutic Agents* (Foye, ed.), Washington, D.C.: American Chemical Society Books, 1995, pp. 9-45; and Weinstein et al., *Science*, 275, 343-349 (1997).

The NCI 60 cell-line human tumor screen measures the ability of a compound to selectively kill or inhibit the growth of diverse human cancers. Generally, in the NCI screen, the compounds of the present invention display potent activity against certain types of human solid tumors (e.g., non-small cell lung cancer, renal cancer, and melanoma), and resistant strains thereof. By these observations, and with other detailed analyses of the characteristic tumor cellular response profiles, it can be shown that the compounds of the present invention have a uniquely characteristic bioactivity profile.

The NCI 60 cell-line human tumor primary screen also provides a means by which to identify natural sources of compounds. The NCI screen was designed and implemented during 1985-1990 under the direction, close scrutiny, and supervision of several internationally comprised and renowned extramural (non-NCI) advisory and review groups, including the NCI Division of Cancer Treatment's Board of Scientific Counselors, an Ad Hoc Expert Review-Committee thereof, the National Cancer Advisory Board, and the President's Cancer Panel (see Boyd, In: *Anticancer Drug Development Guide: Preclinical Screening, Clinical Trials, and Approval* (Teicher, B. A., ed.), Totowa, N.J.: Humana Press, Inc., pp. 23-42, 1997). The impetus for development of the NCI screen was the international recognition that most of the commercially available anticancer drugs worldwide are essentially inactive or only transiently active against most forms of human cancer. Reviews are disclosed, for example, in Boyd, In: *Cancer: Principles and Practice of Oncology Updates* (DeVita, V. T., Jr., et al., eds), Philadelphia: Lippincott, 1989, pp. 11-22; and Boyd, In: *Current Therapy in Oncology* (Niederhuber, J. E., ed.), Philadelphia: BC Decker, 1993, pp. 11-22. Although this NCI screen has been operational only since 1990, it has already led to the discovery, development, and clinical use of significant new anticancer drugs in human cancer patients. For example, see Weinstein et al., *Science*, 275, 343-349 (1997); Greyer and Chabner, In: *Cancer: Principles and Practice of Oncology*, 5th Ed. (DeVita, V. T., et al., eds.), Philadelphia: Lippincott-Raven, 1977, pp. 385-394; and Sausville, In: *Anticancer Drug Development Guide: Preclinical Screening, Clinical Trials, and Approval* (Teicher, B. A., ed.), Totowa, N.J.: Humana Press, Inc., 1997, pp. 217-226.

The NCI screen consists of a panel of 60 different human tumor cell lines against which compounds are tested over a defined range of concentrations to determine the relative degree of growth inhibition or cytotoxicity against each cell line. The design and operation of the screen is such that for each compound tested, both the absolute and relative sensitivities of individual cell lines comprising the screen are sufficiently reproducible that a characteristic profile or "fingerprint" of cellular response is generated. Compounds that are active in the NCI screen show pronounced differential tumor growth-inhibitory and/or cytotoxic effects to the diverse cell lines comprising the 60 cell-line panel. The degree of differential response between the most and least sensitive lines typically may be relatively small (e.g., 2- to 10-fold), or occasionally as great as 3-4 orders of magnitude. Furthermore, the cell lines may be widely heterogeneous in response to a given compound, or they may be comparatively homogeneous, with only a relatively few lines showing much greater or lesser sensitivity than average. Regardless of the magnitude of the differential or the degree of heterogeneity of response of the cell line panel, it is the reproducibility of the response "fingerprint" that is important to the useful information contained therein.

Detailed disclosures of the screening assay are published, for example, in Monks et al., *J. Natl. Cancer Inst.*, 83, 757-766 (1991); Skehan et al., *J. Natl. Cancer Inst.*, 82, 1107-1112 (1990); and Boyd and Paull, *Drug Dev. Res.*, 34, 484-488 (1995). The identities, sources, derivation, morphological, and immunocytochemical characteristics, and methods of maintenance of the cell lines comprising the NCI 60 cell line panel have been described in detail, for example, in Boyd, In: *Cancer: Principles and Practice of Oncology Updates* (DeVita, V. T., Jr., et al., eds), Philadelphia: Lippincott, 1989, pp. 1-12; Monks et al., *J. Natl. Cancer Inst.*, 83, 757-76 (1991); Stinson et al., *Anticancer Res.*, 12, 1034-1035 (1992); and Boyd and Paull, *Drug. Dev. Res.*, 34, 91-109 (1995).

In the screening assay, each agent is tested over a broad concentration range against every cell line in the panel. All lines are inoculated onto a series of standard 96-well microtitre plates on day zero, followed by a 24 h incubation in the absence of the test compound. The inoculation densities employed depend upon the particular cell line and its growth characteristics. Inoculation densities used are as published in Monks et al., *J. Natl. Cancer Inst.*, 83, 757-766 (1991); and Boyd and Paull, *Drug Dev. Res.*, 34, 91-109 (1995). Test compounds are evaluated at five 10-fold dilutions. Following a 48-hour incubation with the test compound, the cells are assayed by the sulforhodamine B procedure as described in Skehan et al., *J. Natl. Cancer Inst.*, 82, 1107-1112 (1990); Monks et al., *J. Natl. Cancer Inst.*, 83, 757-766 (1991); and Rubinstein et al., *J. Natl. Cancer Inst.*, 82, 1113-1118 (1990). Optical densities are measured on automated plate readers, followed by computerized data acquisition, processing, storage, and availability for display and analysis. Each successful test of a compound generates 60 dose-response curves, which are printed in the NCI screening data report as a series of composites comprising the tumor-type subpanels. Data for any individual cell line(s) failing quality control criteria, or otherwise deficient for any cell line(s) not tested successfully, are eliminated from further analysis and are deleted from the screening report.

The "percentage growth" (PG) term, and meaning of the +50, 0, and −50 response reference lines, the calculated response parameters, $GI_{50}$, TGI, and $LC_{50}$, construction and use of "mean-graphs" and the COMPARE pattern-recognition algorithms are briefly summarized as follows. The 50% growth inhibition parameter ($GI_{50}$) is the concentration of test drug where $100 \times (T-T_o)/(C-T_o) = 50 = PG$. The optical density of the test well after the 48 hour drug exposure is T; the optical density at time zero is $T_o$; and the control optical density is C. The PG is a T/C-like parameter that can have values from +100 to −100. Whereas the $GI_{50}$ may be viewed as a growth-inhibitory level of effect, the TGI signifies a "total growth inhibition" or cytostatic level of effect. The TGI is the drug concentration where $100 \times (T-T_o)/(C-T) = 0 = PG$. The $LC_{50}$ is the lethal concentration, "net cell killing" or cytotoxicity parameter. It is the concentration where $100\times(T-T_o)/T_o = -50 = PG$. The control optical density is not used in the calculation of $LC_{50}$. For a detailed description of the "percentage growth" (PG) term, the +50, 0, and −50 response reference lines, the calculated response parameters, $GI_{50}$, TGI, and $LC_{50}$, the construction and use of "mean-graphs," and the COMPARE pattern-recognition algorithms, see Boyd et al., In: *Cytotoxic Anticancer Drugs: Models and Concepts for Drug Discovery and Development* (Valeriote, F. A., et al., eds.), Amsterdam: Kluwer Academic Publishers, 1992, pp. 11-34; Monks et al., *J. Natl. Cancer Inst.*, 83, 757-766 (1991); and Boyd and Paull, *Drug Dev. Res.*, 34, 91-109 (1995).

A mean-graph is a pattern created by plotting positive and negative values, termed "deltas," generated from a set of $GI_{50}$, TGI, or $LC_{50}$ concentrations obtained for a given compound tested against each cell line in the NCI in vitro screen. The deltas are generated from the $GI_{50}$, TGI, or $LC_{50}$ data by a three-step calculation. For example, the $GI_{50}$ value for each cell line successfully tested against a given compound is converted to its $\log_{10} GI_{50}$ value. The mean panel $\log_{10} GI_{50}$ value is obtained by averaging the individual $\log_{10} GI_{50}$ values. Each $\log_{10} GI_{50}$ value then is subtracted from the panel mean to create the corresponding delta.

To construct the mean-graph, the deltas are plotted horizontally in reference to a vertical line that represents the calculated mean panel $GI_{50}$. The negative deltas are plotted to the right of the mean reference line, thereby proportionately representing cell lines more sensitive than the calculated average. Conversely, the positive deltas are plotted to the left of the reference line to represent the less sensitive cell lines to the given agent. Thus, for example, a bar projecting 3 units to the right of the vertical reference line in a $GI_{50}$ mean-graph indicates that the $GI_{50}$ concentration for that cell line is 1000 times less than the panel-averaged $GI_{50}$ concentration. The TGI and $LC_{50}$ mean-graphs are prepared and interpreted similarly.

Three additional numbers are printed at the base of each of the three respective mean-graphs. These numbers are the MG-MID, the Delta (not be confused with the "delta" for an individual cell line), and the Range. The MG-MID is the calculated mean panel $GI_{50}$, TGI, or $LC_{50}$. The Delta is the number of $\log_{10}$ units by which the delta of the most sensitive line(s) of the panel differ(s) from the corresponding MG-MID. Similarly, the Range is the number of $\log_{10}$ units by which the delta of the most sensitive line(s) of the panel differ(s) from the delta(s) of the least sensitive line(s).

COMPARE is a computerized, pattern-recognition algorithm used in the evaluation and exploitation of data generated by the NCI screen. In essence, COMPARE is a method of determining and expressing the degree of similarity, or lack thereof, of mean-graph profiles generated on the same or different compounds. An early impetus for the creation of such a tool during the development of the screen was the need to standardize and to establish and monitor the screen's consistency and reproducibility over time. This is accomplished by the regular testing of standard compounds that are expected to generate the same or very similar profiles when screened repetitively against the same panel of cell lines.

The NCI screen is repetitively calibrated. In the course of standardizing the screen, NCI selected as reference compounds approximately 170 agents for which a considerable amount of information was available about their preclinical and/or clinical anticancer properties and mechanism(s) of action. These compounds included commercially marketed anticancer drugs, investigational anticancer drugs, and other anticancer drugs which were or had been in preclinical development based upon activities in other cancer-related test systems. The repetitive periodic screening of these prototype "standard agents" (the cumulative compilation of results of which forms the "Standard Agents Database") remains the basis for calibration and standardization of the screen.

Significantly, the NCI's Standard Agent Database also provides a key to many useful new drug discovery applications. For example, the characteristic response profile "fingerprint" of a selected standard agent may be used as the "seed" to probe any other available mean-graph database to see if there are any closely matching profiles contained therein. Similarly, a profile selected from any available mean-graph database can be used to probe the "Standard Agent Database" to determine whether or not there are any closely matching standard agent profiles. Additional databases used for such studies may be constructed or defined as desired and may be relatively small (e.g., comprising a single compound or a selected congeneric series of compounds) or very large (e.g., the entire databases from all pure compounds, mixtures, fractions, and extracts tested in the NCI screen to date).

Initial NCI studies with COMPARE showed that compounds with matching mean-graph patterns often had related chemical structures. However, closer examination of this phenomenon revealed that certain compounds of unrelated structures had matching mean-graph patterns and shared the same or related biochemical mechanisms of action. For example, see Boyd, In: *Current Therapy in Oncology* (Niederhuber, J. E., ed.), Philadelphia: B C Decker, 1993, pp. 11-22; and Paull et al., In: *Cancer Therapeutic Agents*, Washington, D.C.: Am. Chem. Soc. Books, pp. 9-45 (1995); and references cited therein. COMPARE analyses can be performed using the mean-graph deltas calculated from either the $GI_{50}$'s, the TGI's, or the $LC_{50}$'s. When a selected particular mean-graph profile or "seed" is used to probe a given database, the appropriate delta value for each cell line is compared to the corresponding delta value for the same cell line for every mean-graph entry in the specified database set. If either delta value is missing for any cell line (e.g., due to test failure or quality control deletion), then that cell line is eliminated entirely from the calculation for that particular seed/mean-graph and database/mean-graph pair. Thus, for each mean-graph in the specified database, a set of pairs (maximum of 60) of delta values is obtained. The commercially available SAS statistical program is used to calculate a Pearson product moment correlation coefficient (0.0-1.0) for each set of delta value pairs. The mean-graphs of all compounds in the specified database can then be rank-ordered for similarity to the seed mean-graph. Public access to the NCI's "Standard Agents Database," as well as to a variety of NCI screening data display and analysis tools, including COMPARE, are available to investigators worldwide via the Internet (http://dtp.nci.nih.gov/).

By regular application of COMPARE, using selected prototype seed compounds from the Standard Agents Database, NCI has maintained ongoing surveillance of the total historical screening database accrued from inception to date. In this manner, compounds with screening fingerprints matching standard agent(s) having known or presumed known mechanism(s) of actions can be identified. NCI has been able to associate and subsequently confirm the database classification of compounds of previously unknown mechanisms of action into a number of different known mechanistic classes of interest. For example, new members have been classified within general mechanistic categories of tubulin-interactive antimitotics, antimetabolites, alkylating agents, topoisomerase inhibitors, DNA binders, and the like. These and numerous other examples resulting from this kind of database prospecting have been published, for example, in Paull et al.,

*Cancer Res.*, 52, 3892-3900 (1992), and references cited therein; and Paull et al., In: *Cancer Chemotherapeutic Agents*, Washington, D.C.: Am. Chem. Soc. Books, 1995, pp. 9-45, and references cited therein.

Quite surprisingly, it has been discovered that, uniquely among the tens of thousands of mean-graph "fingerprints" analyzed by applicants, the characteristic screening "fingerprints" for certain exemplary compounds of the present invention correlate almost perfectly with those of protypical vacuolar-type (H+)-ATPase inhibitory compounds, concanamycin A, bafilomycin A1, salicylihalamide A and lobatamide A, all of which are structurally unrelated to the compounds of the present invention. The correlation for certain exemplary compounds of the present invention is so precise, that the possibility of coincidence is effectively ruled out. It is therefore concluded that the compounds of the present invention, whose mean graph fingerprints in the NCI screen correlate highly with those of concanamycin A, bafilomycin A1, salicylihalamide A, and lobatamide A, are inhibitors of vacuolar-type (H+)-ATPase. Indeed, it can readily be demonstrated by specific vacuolar-type (H+)-ATPase bioassay that compounds of the present invention whose fingerprints in the NCI 60 cell-line screen correlate with those of the structurally unrelated but known vacuolar-type (H+)-ATPase inhibitors (e.g., see Boyd, PCT International Patent Application No. PCT/US00/05582) concanamycin A, bafilomycin A1, salicylihalamide A and lobatamide A have potent vacuolar-type (H+)-ATPase inhibitory activity, as expected. Thus, the NCI 60 cell-line screen can be used to demonstrate that any selected compound of the present invention is an inhibitor of vacuolar-type (H+)-ATPase.

Compounds whose mean-graph "fingerprints" generated by the NCI 60 cell-line screen correlate highly with one another can be expected to share a common molecular target or biological mechanism of action, even if the compounds differ significantly in structure. A high correlation can be established, for example, by COMPARE correlation coefficients of approximately 0.8 to 0.9, or greater. See Boyd, In: *Current Therapy in Oncology* (Niederhuber, J. E., ed.) Philadelphia: B. C. Decker, 1993, pp. 11-22; Boyd and Paull, *Drug Dev. Res.*, 34, 91-109, 1995; Paull et al., In: *Cancer Therapeutic Agents*, Washington, D.C.: Am. Chem. Soc. Books, 1995, pp. 9-45. Thus, the concanamycins, bafilomycins, salicylihalamides and lobatamides, and exemplary compounds of the present invention, for example, whose NCI 60 cell-line screen correlation coefficients with respect to each other are high, can all be shown to share the same molecular target, vacuolar-type (H+)-ATPase. Further illustration of this characteristic is provided in Example 4.

One skilled in the art will appreciate that not all vacuolar-type (H+)-ATPase inhibitors will inhibit equally the vacuolar-type (H+)-ATPase activity present in different kinds or locations of intracellular organelles, or in different kinds or locations of plasma membranes, or in different kinds or locations of cells or tissues. In other words, a given vacuolar-type (H+)-inhibitory compound may preferentially inhibit vacuolar-type (H+)-ATPase activity in one or more kind or location of intracellular organelle, plasma membrane, cell or tissue. Thus, the skilled practitioner will typically select a particular vacuolar-type (H+)-ATPase inhibitory compound for a desired therapeutic use. Compound selection can be based upon the particular kind or location of intracellular organelle or plasma membrane vacuolar-type (H+)-ATPase preferentially inhibited by the compound. Indeed, there are clear precedents in the literature to indicate that compounds can be selected for particular applications based upon preferential inhibition of one or more kind of vacuolar-type (H+)-ATPase over another. For example, Gagliardi et al., *J. Med. Chem.*, 41, 1568-1573, (1998), identified compounds that selectively inhibit human osteoclast vacuolar-type (H+)-ATPase activity compared to human renal cortical vacuolar-type (H+)-ATPase activity; such compounds therefore are expected to be particularly useful in treating osteoporosis.

In addition to the pharmacological utility of inhibitors of mammalian vacuolar-type (H+)-ATPase activity, pharmacological utility may also be obtained by inhibition of non-mammalian vacuolar-type (H+)-ATPase activity. For example, the known vacuolar-type (H+)-ATPase inhibitors bafilomycin $A_1$ and concanamycin A potently inhibit fungal as well as mammalian vacuolar-type (H+)-ATPase activity, and those compounds have strong antifungal activity. See Bowman et al., *Proc. Natl. Acad. Sci. USA*, 85, 7972-7976 (1988); Dröse et al., *Biochemistry*, 32, 3902-3906 (1993); Dröse and Altendorf, *J. Exp. Biol.*, 200, 1-8 (1997).

There is also evidence that vacuolar-type (H+)-ATPase plays important roles in the proliferation of tumor cells, and the consequent invasiveness and metastasis thereof. See Montcourrier et al., *J. Cell Sci.*, 107, 2381-2391 (1994); Martinez-Zaguilan et al., *Am. J. Physiol.*, 265, C1015-C1-29 (1993); Martinez-Zaguilan et al., *J. Cell Physiol.*, 176, 196-205 (1998); Nishihara et al., *Biochem. Biophys. Res. Commun.*, 212, 255-262 (1995); Manabe et al., *J. Cell Physiol.*, 157, 445-452 (1993). Furthermore, acidification of intracellular organelles can contribute to the sequestration and cellular efflux of conventional anticancer drugs. See Marquardt and Center, *J. Natl. Cancer Inst.*, 83, 1098-1102 (1991); Benderra et al., *Intl. J. Oncol.*, 12, 711-715 (1998); Mariyama et al., *J. Biochem.*, 115, 213-218 (1994). Therefore, vacuolar-type (H+)-ATPase inhibitory compounds of the present invention can be used to inhibit the proliferation of tumor cells, as well as the consequent invasiveness and metastasis thereof. Furthermore, the compounds of the present invention can be used to inhibit drug-resistance of tumor cells to conventional anticancer agents.

The particular compound or composition used in accordance with the present invention may be selected based upon the desired kind or site of vacuolar-type (H+)-ATPase inhibition, and/or based upon other pharmacological, toxicological, pharmaceutical or other pertinent considerations that are well-known to those skilled in the art. Routine methods for the specific bioassay, quantitation and comparisons of inhibitory activity of compounds and compositions of the present invention against vacuolar-type (H+)-ATPase activity in various tissues, cells, organelles and other preparations is well-documented in the literature (see, e.g., Bowman et al., *Proc. Natl. Acad. Sci. USA*, 85, 7972-7976 (1988); Gagliardi et al., *J. Med. Chem.*, 41, 1883-1893 (1998); Gagliardi et al., *J. Med. Chem.*, 41, 1568-1573 (1998); and references cited therein).

COMPARE analyses of $GI_{50}$ and TGI mean-graph screening profiles of certain compounds of the present invention can be consistently shown to have a high degree of commonality with respect to each other (e.g., $GI_{50}$ and TGI-COMPARE Pearson correlation coefficients of at least 0.6-0.8 or greater), but do not show any such correlations with any known standard agent. Similarly, extracts of natural organisms, which can be shown to contain compounds of the present invention, typically give $GI_{50}$ and TGI mean-graph screening fingerprints with similarly high $GI_{50}$ and TGI-COMPARE Pearson correlations (e.g., typically 0.6-0.7 or greater) to the compounds of the present invention. This allows a person of skill in the art to readily identify productive source organisms and extracts thereof, from which the skilled artisan can readily obtain and use the compounds of the present invention or precursors thereof. Identification and/or characterization of the present inventive compounds is further facilitated by the presence of certain characteristic NMR signals such as described in Example 2. Such characteristic NMR signals can further confirm the identification and selection of compound mixtures, including crude extracts of natural organisms and partially purified fractions thereof, or synthetic or semi-synthetic reaction products, that contain the compounds.

Certain compounds of the present invention can be readily obtained from natural sources, including solvent extracts of marine sponges, for example, from aqueous extracts of sponge species from the genus *Poecillastra* species. Extracts of *Poecillastra* species sponges can be prepared from any suitable solvent, for example, organic solvents, water, and mixtures thereof. Fresh sponges can be used, but more generally they are frozen immediately after harvesting, and then are either used directly or are freeze-dried before the extraction is done. When a marine sponge is used as a source for obtaining compounds of the present invention, it is preferably from the genus *Poecillastra* species, but is more preferably a *Poecillastra* species, and is most preferably a *Poecillastra* species collected near Settlement Point, Grand Bahama Island, Bahamas (see Example 1).

Specific extracts of *Poecillastra* species that contain compounds of the present invention can be identified and selected based upon the anticancer screening profile they produce in the NCI 60-cell human tumor screen. Such extracts containing compounds of the present invention also can be identified and selected based upon key proton and carbon NMR signals (e.g., see Table 1) that are characteristic of the structural component motif (I) shared by the compounds of the present invention (see also Example 1).

From the aforementioned selected extracts, a variety of methods can be used for isolation and purification of compounds of the present invention. During each step of isolation and purification, the aforementioned characteristic anticancer screening profile or a suitable bioassay, and the aforementioned characteristic proton NMR signals, can be obtained for intermediate fractions, as well as partially purified and purified compounds, to ensure isolation of the desired compounds of the present invention.

A preferred method of obtaining certain compounds of the present invention or a precursor thereof from natural source materials includes the steps of:

(a) obtaining a fresh or frozen sample of a marine sponge (or other suitable natural source material) that includes one or more compounds of the present invention or a precursor thereof, (b) extracting the sample with water and/or one or more organic solvents, or mixtures thereof, which dissolves the compound(s) or precursor(s) to form an extract, (c) optionally treating the extract with a solvent (e.g., a nonsolvent such as ethanol) to precipitate and remove high molecular weight proteins and sulfated polysaccharides, (d) optionally partitioning the extract between an organic solvent and an aqueous solvent to form a partitioned organic solvent extract or aqueous solvent extract containing the desired compound(s) or precursor(s), (e) chromatographing, one or more times as necessary, the partitioned extract, for example, on an adsorption, partition, or reversed-phase, or size-exclusion matrix, to produce one or more fractions, and (f) isolating one or more compounds of the present invention or one or more precursors thereof from one or more of the fractions.

In step (b), the solvent can include mixtures of suitable nonpolar organic solvents or suitable polar organic solvents. Suitable nonpolar organic solvents include, for example, $CH_2Cl_2$, $CHCl_3$, toluene, hexane and the like. Suitable polar organic solvents include, for example, water, MeOH, EtOH, isopropyl alcohol, acetone and the like. In step (d) suitable organic nonpolar solvents include $CH_2Cl_2$, hexane, $CCl_4$, $CHCl_3$, MeOtBu, ethyl acetate and the like; and typical aqueous solvents can include, for example, mixtures of water and methanol. Non-limiting examples of solvent mixtures that can be used optionally in this partitioning step include: (1) $CH_2Cl_2$ and 19:1 $H_2O$-MeOH, (2) hexane and 9:1 MeOH—$H_2O$, (3) $CCl_4$ and 8:2 MeOH—$H_2O$, (4) $CH_2Cl_2$ and 7:3 MeOH—$H_2O$, and (5) EtOAc and $H_2O$.

In step (e), the chromatography preferably is column chromatography. When column chromatography is used, the chromatographic matrix preferably is the adsorption type, the partition type, the reversed-phase type, the size exclusion type, or a suitable combination thereof. Preferably, the solvent and/or the matrix is not acidic in nature when the compound to be isolated is not particularly acid stable. Sephadex™ LH-20, a particularly preferred matrix for isolation of certain types of compounds of the present invention, combines three of the aforesaid matrix types, and is characterized by mild treatment and good recoveries.

The isolation step (f) can be carried out, for example, by evaporating the solvent, by recrystallization optionally after additional concentration using reversed-phase HPLC, or by using other isolation procedures known in the art.

In a preferred isolation method, a selected sample of frozen *Poecillastra* species sponge is ground to a powder with dry ice. The dry ice is allowed to sublime, distilled $H_2O$ is added, and the thawed material is stirred for 3 h at 3° C., and then centrifuged. The aqueous supernatant is lyophilized and the concentrated extract is fractionated on wide-pore reversed-phase $C_4$ media. The fraction eluting with MeOH—$H_2O$ (2:1) is further separated on an LH-20 column using a MeOH:$H_2O$ (7:3) solvent system. The early eluting material from this column is ultimately purified by reversed-phase $C_{18}$ HPLC with a linear $CH_3CN$—$H_2O$ gradient (with or without the addition of about 0.01% trifluoroacetic acid) to give, after solvent removal, substantially purified compound(s) of the present invention.

The definitive proofs of structure of the isolated compounds can be obtained by a combination of methods including primary spectral analyses (e.g., high-resolution NMR and mass spectrometry, infrared and UV spectroscopy), comparisons of spectral and physico-chemical properties with related literature precedents, and by x-ray crystallographic analysis. Various structural proofs are illustrated in Example 2 herein.

The following examples further illustrate the invention but, of course, should not be construed as in any way limiting its scope.

EXAMPLES

High performance liquid chromatography (HPLC) was performed on a Varian-Rainin system employing a Dynamax $C_{18}$ column (1×25 cm), using a flow rate of 3 mL/minute and ultraviolet (UV) detection at 220 nm. Optical rotations were measured with a Perkin-Elmer 241 polarimeter. UV and infrared (IR) spectra were obtained on a Beckman DU-640 and a Perkin-Elmer 1600 FT-IR spectrometer, respectively. High resolution mass spectra were acquired on a JEOL SX102 mass spectrometer.

Nuclear magnetic resonance (NMR) spectra were recorded at 29° C. on 800 μg of poecillastrin A (1) dissolved in 180 μL of DMF-$d_7$ and placed in a 3 mm NMR tube. The heteronuclear multi-bond connectivity (HMBC) data were collected on a Varian INOVA 500 spectrometer outfitted with a 5 mm HCN inverse-detection Chili-Probe. The radio frequency coils and preamplifier of the Chili-Probe were cooled with liquid helium to approximately 25 K and 60 K, respectively. The HMBC, which was optimized for $^1J_{CH}$=140 Hz and $^nJ_{CH}$=6 Hz, was acquired in approximately 32.5 hrs with 1,025 (F2)×256 (F1) points (all data points reported represent complex data points), 256 scans per increment, and F2 and F1 spectral widths of 6,000 and 27,036, respectively. The F1 dimension was zero-filled to 2K and the data was processed with a sinebell weighting function. All other NMR data were obtained on a Varian INOVA 800 spectrometer equipped with a 3 mm inverse-detection probe operated at room temperature. An absolute value correlated spectroscopy spectrum (COSY) was acquired with 2K (F2)×192 (F1) points, 16 scans per increment, and 8468 Hz spectral width in both dimensions. The total correlation spectroscopy (TOCSY) data were acquired with a 60 ms mixing time at 8.3 KHz field strength, 1K×224 points, 16 scans per increment, and 6,000 Hz spectral width in both dimensions. The rotating-frame Overhauser enhancement spectroscopy (ROESY) was acquired with a 300 ms mixing time at 5.5 KHz field strength, 2K×256 points, 16 scans per increment, and 8,468 Hz spectral width in both dimensions. The multiplicity-edited HSQC, with $^1$JCH=140 Hz, was acquired with 1,536×256 points, 192 scans per increment, and spectral widths of 8,468 Hz in F2 and 28,139 Hz in F1. The COSY data were processed with a sinebell weighting function and gaussian weighting was used for the other data sets obtained at 800 MHz. All of these experiments had the F2 dimension zero-filled to 4K, except for the heteronuclear single quantum correlation (HSQC), which was zero-filled to 2K. The F1 dimension of the HSQC and COSY were zero-filled to 1K, while in the TOCSY and ROESY, F1 was zero-filled to 512. Two- and three-fold linear predictions were performed on the HSQC and COSY data, respectively. Chemical shifts are reported in ppm relative to the residual nondeuterated solvent. Assignments for the $^{13}$C resonances were based on HSQC and HMBC correlations, and their multiplicities were inferred from the multiplicity-edited HSQC experiment.

Samples of the sponge *Poecillastra* species were collected by a manned submersible at a depth of −359 meters near Settlement Point, Grand Bahama Island, Bahamas. A voucher specimen (# Q66B974) for this collection is maintained at the Smithsonian Institution, Washington, D.C.

Example 1

This example describes the isolation and purification of poecillastrin A (1). The frozen *Poecillastra* sponge (394 g) was ground to a fine powder and extracted with H$_2$O to give 94 g of aqueous extract. After numerous chemical separation schemes were attempted, the following bioassay-guided isolation procedure was employed. A 20 g portion of the extract was dissolved in 120 mL of H$_2$O and precipitated by addition of 120 mL of ethanol (EtOH) and storage at −20° C. for 16 h. After removal of the precipitate by centrifugation, the supernatant was evaporated to dryness and then partitioned between H$_2$O and normal-butanol (n-BuOH). The n-BuOH soluble material (1.03 g) was triturated with MeOH to give a 917 mg methanol (MeOH)-soluble fraction. Separation of this material on a Sephadex LH-20 column eluted with MeOH—H$_2$O (7:3) provided a cytotoxic fraction (43 mg) that was chromatographed on a second Sephadex LH-20 column eluted with 100% MeOH. The cytotoxic fractions from this LH-20 column were combined to give 12.1 mg of material that was subjected to C$_{18}$ column chromatography eluted with MeOH—H$_2$O (2:3). Final purification was achieved by C$_{18}$ HPLC eluted with a linear gradient of CH$_3$CN—H$_2$O (9:11) to 100% CH$_3$CN (0.1% TFA vol/vol in the eluant) over 45 min to give 800 μg of poecillastrin A (1).

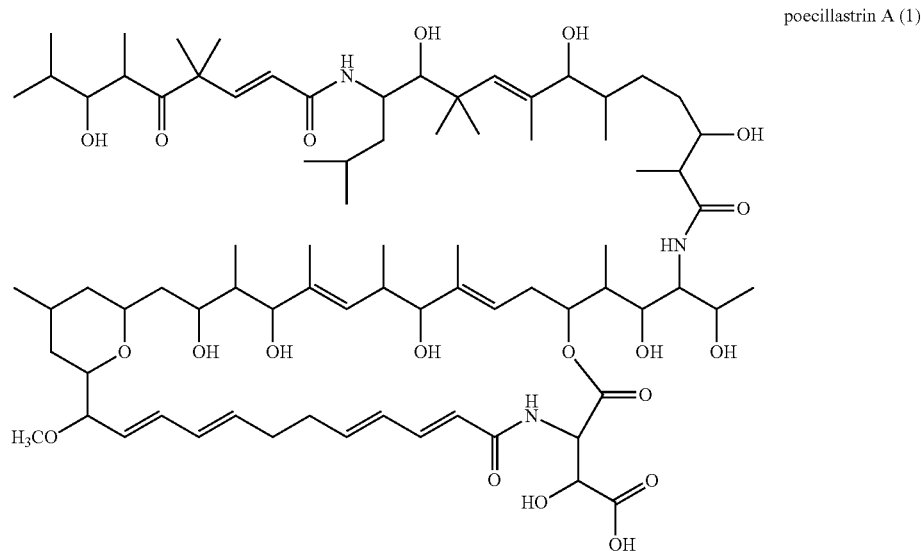

poecillastrin A (1)

Example 2

This example demonstrates the structural proofs of particular compounds of the present invention.

Poecillastrin A (1), such as obtained in Example 1, was a white gum with the following spectral characteristics: UV [MeOH] λ$_{max}$ 229 (ε 10,800), 235 (ε 10,900), 263 (ε 10,200) nm; IR υ$_{max}$ (neat on a NaCl plate) 3500-3300, 1716, 1697, 1683, 1206, 1135 cm$^{-1}$; $^1$H and $^{13}$C NMR data, see Table 1; Fast atom bombardment mass spectrometry (FABMS) (M+Na)$^+$ m/z 1464.9; High resolution fast atom bombardment mass spectrometry (HRFABMS) of a CsI-doped sample, (M-H+2Cs)$^+$ m/z 1706.7375, calcd for C$_{79}$H$_{130}$N$_3$O$_{20}$Cs$_2$, 1706.7350. An accurate determination of the optical rotation was difficult due to the limited sample size. Forty-two individual measurements were made and all of them provided negative optical rotations. The optical rotation calculated for 1 was based on the average of these forty two measurements: $[\alpha]^{27}_D$ −8.3° (c 0.056, MeOH).

The molecular formula of 1 was established to be $C_{79}H_{131}N_3O_{20}$ by HRFAB MS measurements. A 180 μL sample of 1 in DMF-$d_7$ was prepared and $^1$H, COSY, TOCSY, ROESY, and HSQC NMR data were obtained at 800 MHz using a 3 mm room temperature probe. HMBC data, which were required for the structural elucidation of 1, were acquired at 500 MHz using a 5 mm HCN inverse-detection Varian Chili-Probe in which the radio frequency coils and preamplifier were cooled to approximately 25 K and 60 K, respectively. The NMR data (Table 1) established that poecillastrin A (1) was a new, highly functionalized macrolide, structurally related to the chondropsins (Cantrell et al., *J. Am. Chem. Soc.* 2000, 122, 8825-8829; Rashid et al., *Tetrahedron Lett.* 2001, 42, 1623-1626; Rashid et al., *J. Nat. Prod.* 2001, 64, 1341-1344).

The portion of 1 from C-5 to C-24 contained a chain of 20 contiguous protonated carbons, and it was possible using the 800 MHz NMR data to assemble this structural fragment along with the associated methyl and oxygenated substituents. The section of 1 that encompassed C-25 to C-29 was assigned by proton-proton spin system analysis and HMBC data. The spin system that extended from C-30 through to C-68 was assigned in a similar manner. No vicinal coupling was observed between the protons on C-41 and C-42, so ultimately the connection between C-41 and C-42 was assigned, based on ROESY interactions observed between H-41 and H-67. The C-32 oxymethine proton had a downfield chemical shift ($\delta_H$ 5.26), which indicated that the oxygen at position 32 was esterified. This was confirmed by an HMBC correlation from H-32 to an ester carbonyl at $\delta_C$ 172.1. COSY and HMBC correlations established that the ester carbonyl was part of an amino malic acid moiety that was attached to C-4 ($\delta_C$ 166.6) via an amide bond. Thus, poecillastrin A (1) contains a 33-membered macrocyclic ring that incorporates an amide bond between N-3 and C-4, and an ester link between C-1 and the oxygen on C-32. An HMBC correlation from the N-43 proton ($\delta_H$ 7.38) to the C-44 carbonyl ($\delta_C$ 176.7) defined another amide linkage, while homonuclear proton couplings and HMBC data allowed extension of the acyclic portion of 1 out through the gem dimethyl substituents on C-75. The remaining structural fragment from C-57 to C-65 was assembled using proton coupling data to define the spin systems and HMBC correlations to bridge the nonprotonated carbons. Attachment of this fragment through an α,β-unsaturated amide bond was established by HMBC correlations from both NH-56 ($\delta_H$ 7.70) and H-59 ($\delta_H$ 6.90) to C-57 ($\delta_C$ 164.8). The geometry of the olefin bonds in 1 were assigned as all E based on proton-proton couplings and ROESY interactions. Stereochemical assignments for 1 were not attempted due to the large number of asymmetric carbons (24) in the molecule and the small sample size.

TABLE 1

$^1$H and $^{13}$C NMR Data for Poecillastrin A (1) in DMF-$d_7^a$

| position | $d_C$ mult | $d_H$ mult (J in Hz) | HMBC | position | $d_C$ mult | $d_H$ mult (J in Hz) | HMBC |
|---|---|---|---|---|---|---|---|
| 1 | 172.1 s | | | 42 | 54.7 d | 3.89 dd (9.0, 4.0) | C-67 |
| 2 | 56.3 d | 5.10 dd (9.5, 2.2) | C-34 | 43 | | 7.38 d (9.0) | C-44 |
| 3 | | 8.21 d (9.5) | C-4 | 44 | 176.7 s | | |
| 4 | 166.6 s | | | 45 | 47.2 d | 2.50 pent (7.0) | C-44, C-46, C-47, C-69 |
| 5 | 124.0 d | 6.34 d (15.2) | C-4, C-7 | 46 | 74.1 d | 3.51 m | C-44, C-69 |
| 6 | 141.3 d | 7.12 dd (15.2, 11.0) | C-4, C-5, C-7, C-8 | 47 | 33.5 t | 1.51 m, 2H | |
| 7 | 129.8 d | 6.26 m | C-5, C-8, C-9 | 48 | 30.2 t | 1.29 m, 2H | |
| 8 | 142.0 dt | 6.08 d (15.0, 10.4) | C-6, C-9 | 49 | 36.5 d | 1.56 m | |
| 9 | 33.9 t | 2.23 m, 2.31 m | | 50 | 83.5 d | 3.57 m | C-52, C-71 |
| 10 | 32.8 t | 2.19 m, 2H | | 51 | 136.1 s | | |
| 11 | 134.5 d | 5.82 dt (15.0, 8.0) | | 52 | 135.1 d | 5.47 bs | C-50, C-54, C-71, C-72, C-73 |
| 12 | 131.2 d | 6.25 m | C-10, C-14 | 53 | 40.8 s | | |
| 13 | 134.5 d | 6.36 dd (15.2, 11.0) | C-11, C-15 | 54 | 81.7 d | 3.51 m | C-52, C-55, C-74 |
| 14 | 131.5 d | 5.54 dd (15.2, 8.3) | C-12 | 55 | 50.3 d | 4.18 m | |
| 15 | 80.9 d | 3.98 m, | C-13, C-16, OCH$_3$ | 56 | | 7.70 d (9.6) | C-55, C-57 |
| 16 | 75.5 d | 3.55 m | C-15, C-18, C-20 | 57 | 164.8 s | | |
| 17 | 34.4 t | Hb 1.14 m, Ha 1.86 m | | 58 | 124.7 d | 6.16 d (15.2) | C-57, C-60 |
| 18 | 26.0 d | 1.85 m | | 59 | 146.8 d | 6.90 d (15.2) | C-57, C-58, C-60, C-61, C-79 |
| 19 | 41.5 t | Hb 0.80 m, Ha 1.57 m | | 60 | 51.2 s | | |
| 20 | 68.5 d | 3.55 m | | 61 | 215.3 s | | |
| 21 | 43.6 t | 1.29 m, 1.43 m | | 62 | 44.8 d | 3.15 dq (9.6, 7.0) | C-61, C-63, C-80 |
| 22 | 66.1 d | 4.18 m | | 63 | 77.7 d | 3.52 m | |
| 23 | 41.6 d | 1.45 m | | 64 | 29.8 d | 1.74 m | C-65, C-81 |
| 24 | 80.1 d | 3.82 d (9.6) | C-22, C-23, C-26, C-37 | 65 | 14.2 q | 0.82 d (7.0), 3H | C-63, C-64, C-81 |
| 25 | 138.1 s | | | 66 | 10.1 q | 0.94 d (7.0), 3H | C-32, C-40, C-41 |
| 26 | 136.1 d | 5.17 bd (8.0) | C-24, C-37 | 67 | 70.6 d | 3.99 m | |
| 27 | 37.1 d | 2.56 m | | 68 | 20.8 q | 1.11 d (6.0), 3H | C-42, C-67 |
| 28 | 81.7 d | 3.65 d (9.0) | C-26, C-27, C-29, C-30 | 69 | 15.9 q | 1.16 d (7.0), 3H | C-44, C-45, C-46 |
| 29 | 138.9 s | | | 70 | 15.6 q | 0.90 d (7.0), 3H | C-48, C-49, C-50 |
| 30 | 122.0 d | 5.27 m | C-28, C-39 | 71 | 13.7 q | 1.65 s, 3H | C-50, C-51, C-52 |
| 31 | 31.1 t | 2.35 m, 2H | C-29, C-30, C-32 | 72 | 25.4 q | 1.10 s, 3H | C-52, C-53, C-54 |
| 32 | 75.3 d | 5.26 m | C-1, C-41, C-66 | 73 | 26.9 q | 1.18 s, 3H | C-52, C-53, C-54 |
| 33 | 73.3 d | 4.87 d (2.2) | C-1 | 74 | 40.8 t | 1.46 m, 1.54 m | |
| 34 | 171.7 s | | | 75 | 25.3 d | 1.53 m | |
| 35 | 22.9 q | 0.88 d (6.5), 3H | C-17, C-18, C-19 | 76 | 24.5 q | 0.84 d (7.0), 3H | C-74, C-75, C-77 |
| 36 | 10.0 q | 0.60 d (6.8), 3H | C-22, C-23, C-24 | 77 | 21.8 q | 0.86 d (7.0), 3H | C-74, C-75, C-76 |
| 37 | 11.4 q | 1.60 s, 3H | C-24, C-25, C-26 | 78 | 23.7 q | 1.21 s, 3H | C-59, C-60, C-61 |

TABLE 1-continued

$^1$H and $^{13}$C NMR Data for Poecillastrin A (1) in DMF-d$_7$[a]

| position | d$_C$ mult | d$_H$ mult (J in Hz) | HMBC | position | d$_C$ mult | d$_H$ mult (J in Hz) | HMBC |
|---|---|---|---|---|---|---|---|
| 38 | 17.8 q | 0.76 d (6.8), 3H | C-26, C-27, C-28 | 79 | 23.9 q | 1.27 s, 3H | C-59, C-60, C-61, C-78 |
| 39 | 12.3 q | 1.59 s, 3H | C-28, C-29, C-30 | 80 | 15.7 q | 0.83 d (7.0), 3H | C-61, C-62, C-63 |
| 40 | 40.3 d | 1.84 m | | 81 | 20.7 q | 0.92 d (7.0), 3H | C-63, C-64, C-65 |
| 41 | 74.3 d | 3.66 m | | OCH$_3$ | 56.4 q | 3.23 s, 3H | C-15 |

[a]$^{13}$C assignments were made using HSQC and HMBC data, and multiplicities inferred using a multiplicity-edited HSQC pulse sequence.

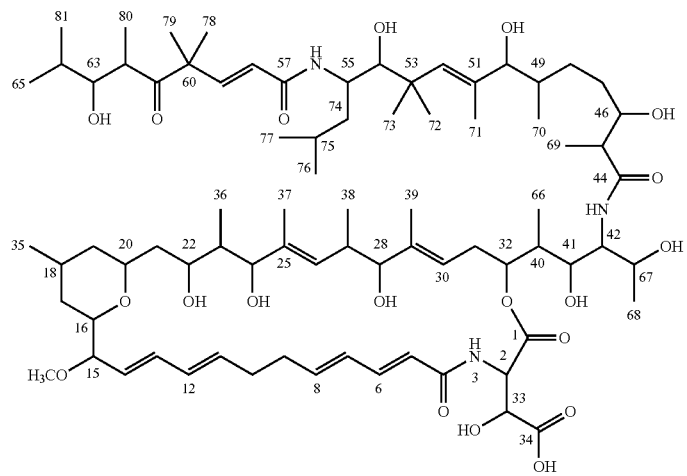

1

Example 3

This example illustrates the general procedure for obtaining the activity profile of compounds of the present invention using the NCI 60 cell-line screen.

An extract from *Poecillastra* species was tested in the NCI 60 cell-line screen as described in detail in Boyd and Paull, *Drug Dev. Res.*, 34, 91-109 (1995); and Monks et al., *J. Natl. Cancer Inst.*, 83, 757-766 (1991). Briefly, a stock solution of the extract was prepared initially in dimethylsulfoxide at 400× the desired final highest test concentrations and stored at −70° C. until use. The final highest test concentrations studied in this example varied between $10^{-5}$ and $10^{-8}$ molar. At the time of screening, an aliquot of the thawed stock was diluted with complete medium containing 50 μg/ml gentamycin to give a concentration of 2× the desired final highest test concentration. Four additional 10-fold serial dilutions were then made to provide a total of five concentrations, spanning a 4-log$_{10}$ concentration range. One hundred μl aliquots of these intermediate dilutions were immediately added to the appropriate microtitre wells, each already containing the appropriate numbers and types of cells in 100 μl of culture medium, resulting in the desired five final concentrations.

The 60 cell lines used, and the respective inoculation densities, were as described in Boyd and Paull, supra, and Monks et al., supra. Following the compound additions, the plates were incubated for 48 h at 37° C. under a 5% CO$_2$/air atmosphere and 100% humidity. Then, adherent cells (all lines except the leukemia) were fixed in situ by gentle addition of cold trichloroacetic acid (50 μl of 50% w/v) and incubated for 60 min at 4° C. Supernatants were discarded, and plates were washed five times with deionized water and air-dried. Sulforhodamine B solution (SRB; 100 μl at 0.4% w/v in 1% acetic acid) was added to each plate, followed by further incubation for 10 min at room temperature. Excess unbound dye was then removed by washing five times with 1% acetic acid, followed by air-drying. The bound stain in each well was solubilized by addition of 100 μl of 10 mM unbuffered Tris base; this was followed by a determination of optical densities (515 nm) on an automated plate reader. For suspension cell cultures (the leukemias), the method was the same except that, at the end of the drug incubation period, the settled cells were fixed in situ to the bottoms of the microtitre wells by gentle addition of 50 μl of 80% trichloroacetic acid. Appropriate control wells were included in the test plate format (Monks et al., *J. Natl. Cancer Inst.*, 83, 757-766 (1991)) to allow subtraction of background optical densities, drug-blank corrections, and a determination of cell densities at time 0 (the time at which compounds are added).

Figure 1B:
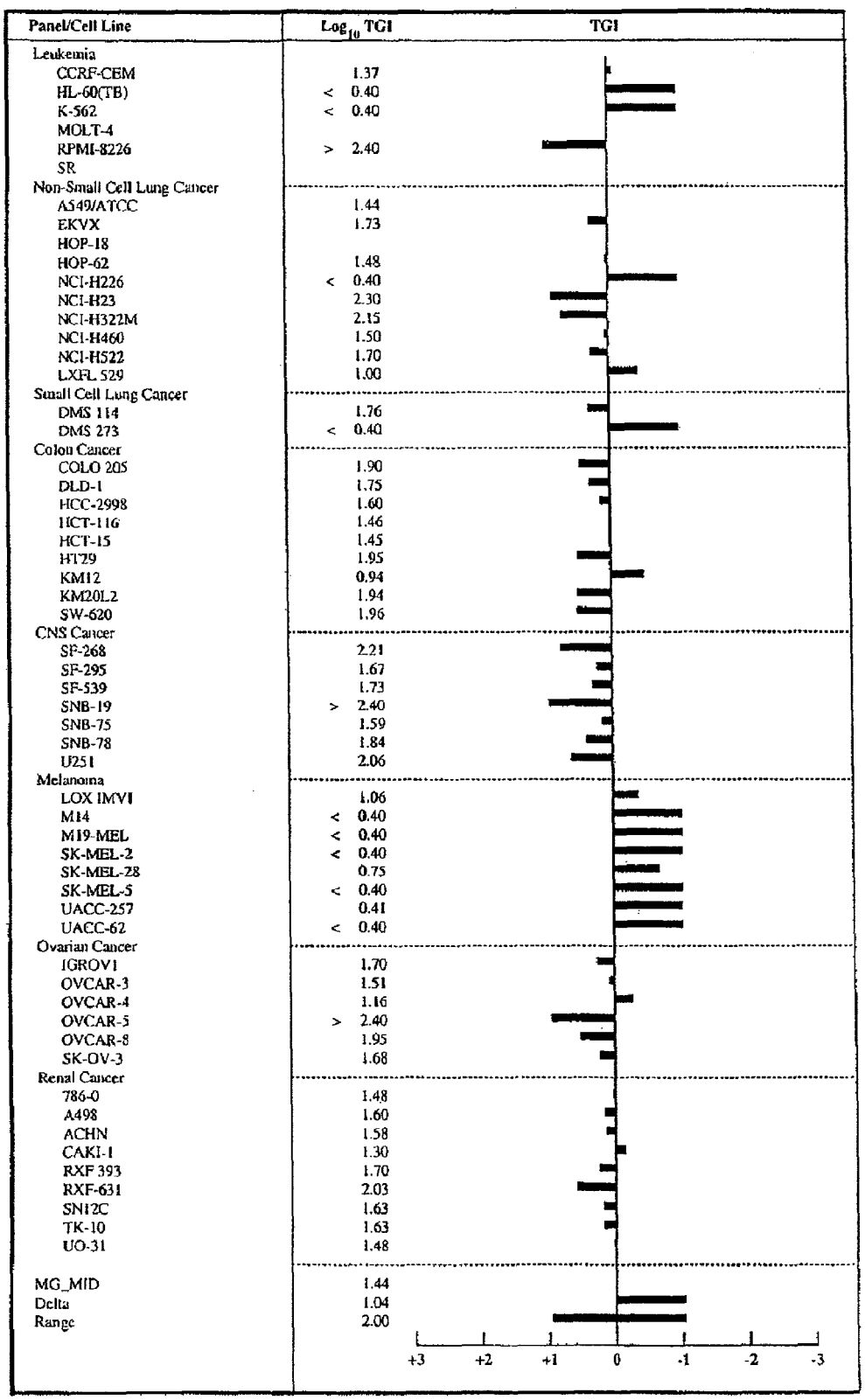
FIG. 1B illustrates the TGI-based mean-graph "fingerprint" of an extract of Poecillastra species in the NCI 60 cell-line screen.
Figure 1C:
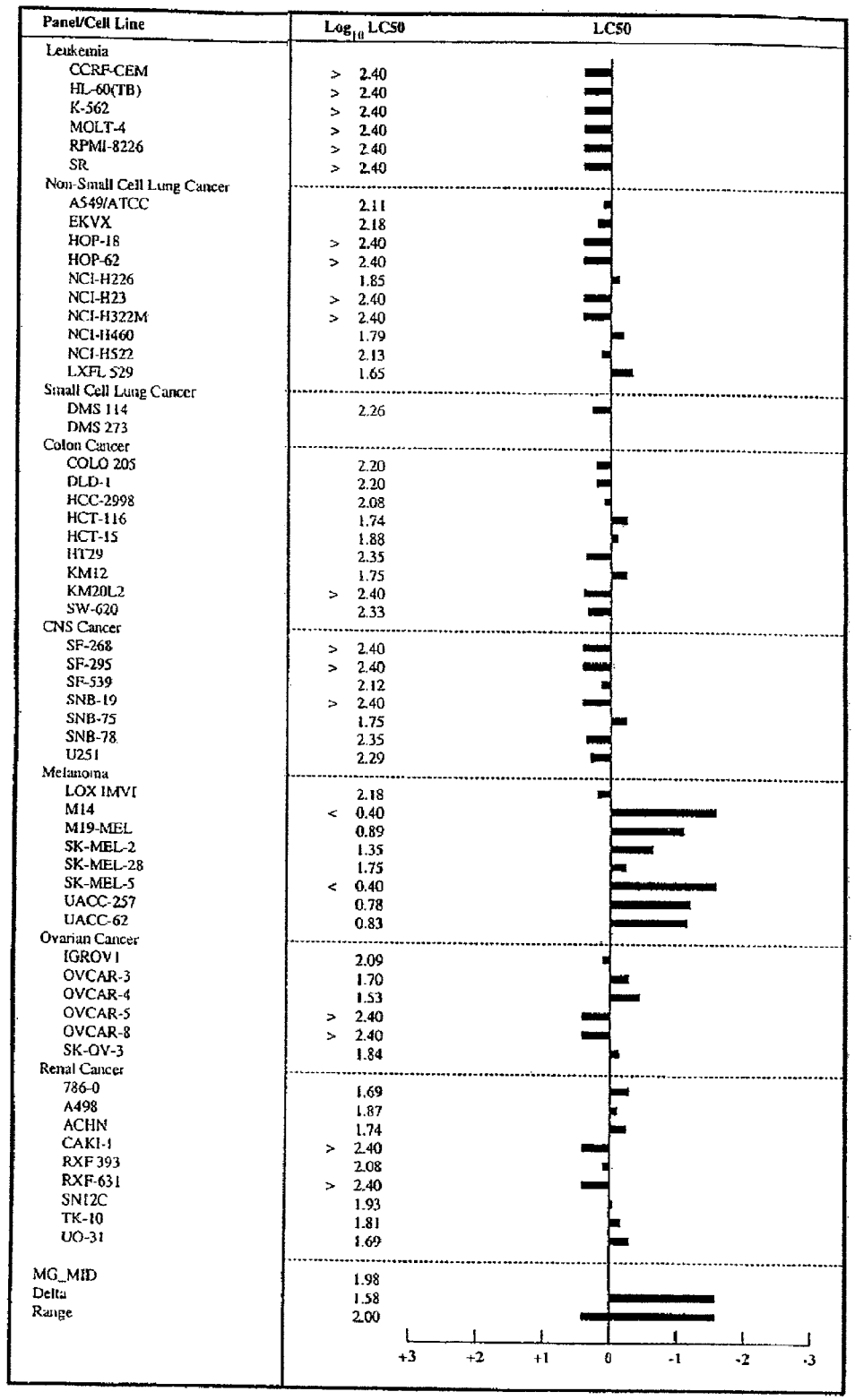
FIG. 1C illustrates the $LC_{50}$-based mean-graph "fingerprint" of an extract of Poecillastra species in the NCI 60 cell-line screen.

The testing of extract of *Poecillastra* species in the NCI 60 cell-line screen gave the characteristic GI$_{50}$-based and TGI-based mean-graph "fingerprints" in the NCI 60-cell screen exemplified in FIGS. 1A, 1B and 1C. The following averaged, individual negative log$_{10}$ GI$_{50}$ values, shown along with the respective subpanel and cell-line identifiers, were recorded for the extract of *Poecillastra* species (of which poecillastrin A is a major component): (Leukemia) CCRF-CEM (<0.40), HL-60-TB (<0.40), K-562 (<0.40), MOLT-4 (<0.40), RPMI-8226 (1.89), SR (<0.40); (Non-Small Cell Lung) A549/ATCC (<0.40), EKVX (1.34), HOP-18 (1.30), HOP-62 (<0.40), NCI-H226 (<0.40), NCI-H23 (1.87), NCI-H322M (1.87), NCI-H460 (<0.40), NCI-H522 (0.73), LXFL529 (<0.40); (Small Cell Lung) DMS114 (0.97), DMS273 (<0.40); (Colon) COL0205 (<0.40), DLD-1 (1.11), HCC-2998 (<0.40), HCT-116 (<0.40), HCT-15 (<0.40), HT29 (<0.40), KM12 (<0.40), KM20L2 (<0.40), SW-620 (<0.40); (CNS) SF-268 (1.55), SF-295 (<0.40), SF-539 (1.42), SNB-19 (2.01), SNB-75 (1.44), SNB-78 (1.55), U251 (1.63);

(Melanoma) LOX-IMVI (<0.40), MALME-3M (<0.40), M14 (<0.40), SK-MEL-2 (<0.40), SK-MEL-28 (<0.40), SK-MEL-5 (<0.40), UACC-257 (<0.40), UACC-62 (<0.40); (Ovary) IGROV1 (1.45), OVCAR-3 (1.11), OVCAR-4 (<0.40), OVCAR-5 (1.97), OVCAR-8 (<0.40), SK-OV-3 (1.51); (Renal) 786-0 (0.95), A498 (1.02), ACHN (1.42), CAKI-1 (0.97), SN-12C (1.02), TK-10 (1.45), UO-31 (<0.40).

$GI_{50}$ and TGI-COMPARE analyses of the full data set obtained from the screening of the extract of *Poecillastra* species revealed that the compound gave a striking pattern of differential cytotoxicity in the NCI 60 cell-line screen that is characteristic of compounds of the present invention (e.g., Pearson correlation coefficients greater than or equal to 0.7-0.8) but unlike that of any known conventional anticancer drug class.

Example 4

This example demonstrates the vacuolar-type (H+)-ATPase inhibitory activity of an extract of *Poecillastra* species.

This method employs the NCI 60 cell-line in vitro screen to obtain a mean-graph "fingerprint" of a desired mechanistic prototype compound, then using a computer-based search algorithm called COMPARE, to search a database of mean-graph "fingerprints" of structurally unrelated compounds to thereby identify compounds with fingerprints very similar, if not indistinguishable, from that of the selected prototype (or "seed"). The degree of similarity is determined by calculation of a COMPARE correlation coefficient, which can vary from a lowest value of zero (which indicates no correlation), to a highest value of one (which indicates a perfect correlation). A high COMPARE correlation (i.e., indicating a high degree of similarity) between the mean-graph "fingerprints" of different compounds indicates that the compounds act on the same or similar molecular target and, therefore, share essentially the same or similar mechanism of biological activity. In practical terms, a COMPARE correlation coefficient of about 0.9 or higher indicates that, within the limits of experimental error of the screening process, the mean-graph "fingerprints" of the compared compounds are essentially identical or indistinguishable and, therefore, that the compounds act on the same molecular target. For pertinent background on the NCI 60 cell-line screen and the method and applications of COMPARE, see Boyd, In: *Current Therapy in Oncology* (Niederhuber, J. E., ed) Philadelphia: B. C. Decker, 1993, pp. 11-22; Boyd and Paull, supra; Paull et al., In: *Cancer Chemotherapeutic Agents*, Washington, D.C.: Am. Chem. Soc. Books, 1995, pp. 11-45.

Potent known vacuolar-type (H+)-ATPase inhibitors, (see, e.g., Boyd, PCT International Patent Application No. PCT/US00/05582), lobatamide A, bafilomycin $A_1$, concanamycin A and salicylihalamide A were selected for use as comparative examples. For pertinent background on concanamycins and bafilomycins, see Bowman et al., *Proc. Natl. Acad. Sci. USA*, 85, 7972-7976 (1988); Dröse et al., Biochemistry, 32, 3902-3906 (1993); Dröse and Altendorf, *J. Exp. Biol.*, 200, 1-8 (1997). For pertinent background on lobatamide A and salicylihalamide A, see Boyd, PCT International Patent Application No. PCT/US00/05582.

In the present example, authentic, well characterized and documented reference samples of concanamycin A and bafilomycin $A_1$ were obtained from a commercial supplier (Kamiya Biochemical Company, Tukwila, Wash.). Salicylihalamide A and lobatamide A were obtained as described by Boyd, PCT International Patent Application No. PCT/US00/05582.

As appropriate for this demonstration, the TGI meangraph, derived from the contemporaneous testing of an extract of *Poecillastra* species, was used as the "seed" to search against the TGI mean-graphs and $LC_{50}$ mean-graphs contained in the aforementioned database, and as the basis for calculation of the COMPARE coefficients.

Table 2 summarizes the TGI-COMPARE and $LC_{50}$-COMPARE correlation coefficients from the testing of lobatamide A, concanamycin A, bafilomycin $A_1$, salicylihalamide A and an extract of *Poecillastra* species in the NCI 60 cell-line screen. The mean-panel $GI_{50}$ values are also shown in Table 2.

TABLE 2

| Compound | TGI-COMPARE Correlation Coefficient | $LC_{50}$'s |
|---|---|---|
| Lobatamide A | 0.50 | 0.66 |
| Concanamycin A | 0.43 | 0.47 |
| Bafilomycin $A_1$ | 0.54 | 0.65 |
| Salicylihalamide A | 0.61 | 0.60 |
| Extract of *Poecillastra* species | 1.00 | 1.00 |

As shown in Table 2, this analysis correctly identified compounds which, although structurally distinct from the seed, nonetheless shared the same molecular target (i.e., in this instance, vacuolar-type (H+)-ATPase). Compounds of the present invention can exhibit a range of relative absolute potencies against vacuolar-type (H+)-ATPase.

Example 5

This example describes the cytoxicity of poecillastrin A (1), isolated in Example 1. The cytotoxicity assay, details of which have been described previously (Bokesch et al., *J. Nat. Prod.* 1999, 62, 633-635), utilized melanoma (LOX), breast (A-549), ovarian (OVCAR-3), and non-small cell lung (SNB-19) human tumor cell lines and IC-2$^{WT}$ and IC-2$^{V814}$ murine mast cell lines (Hashimoto et al., *Am. J. Pathol.* 1996, 148, 189-200).

The in vitro 10 cell-line bioassay was a two day bioassay. Cells were grown in RPMI-1640 (Roswell Park Memorial Institute) without L-glutamine, supplemented with 10% fetal bovine serum, 5.0 mL of a 200 mM glutamine stock, and 0.5 mL of gentamicin and plated out in T-162 cm$^2$ flasks. Once the cells were confluent, they were harvested and plated in 96-well microtiter flat-bottom plates at a seeding density of 50-10,000 cells per well, to yield optical density readings in the range of 1-2.0, and incubated for 1 h in a 37° C., 5% $CO_2$ incubator. After the 1 h incubation, the cells were then introduced to the sample of poecillastrin A, via a Beckman Biomek Workstation-1000. The Biomek-1000 performed seven serial dilutions in a 96-well round-bottom plate and then transferred aliquots of 100 μL to the assay plate. The plate was then returned to the incubator for 24 h. After the two day incubation, the cells were exposed to tetrazolium salt, 2,3-bis[2-methoxy-4-nitro-5-sulfophenyl]-2H-tetrazolium-5-carboxanilide (XTT), for a 4 h incubation in a 37° C. incubator, where viable cells reduced the tetrazolium salt to a colored formazan product. Once the incubation was complete, the plates were read in a dual wavelength mode at 450 nm, with a 650 nm reference, using a SpectraMAX 250 (Molecular Devices) plate reader. Resulting data for each cell line are found in Table 3.

TABLE 3

| Tumor Type | Cell Line | IC$_{50}$ (µM) |
|---|---|---|
| Melanoma | LOX | 0.014 |
| Ovarian | OVCAR-3 | 0.028 |
| Breast | A549 | >10 |
| Non-small cell lung | SNB-19 | >10 |
| Murine mast cell | IC-2 WT | 0.206 |
| Murine mast cell | IC-2 V814 | 0.546 |

The data confirm that poecillastrin A is both a potent and differential cytotoxin, similar to the chondropsins.

Example 6

This example demonstrates the vacuolar-type (H+)-ATPase inhibitory activity of poecillastrin A using a vacuolar-type (H+)-ATPase inhibition assay.

Poecillastrin A was tested for its inhibitory activity against vacuolar-type (H+)-ATPases from bovine chromaffin granule membranes ("Bovine CGM V-ATPase") and from vacuolar membranes of *N. crassa* ("Nc VM V-ATPase"). For Nc VM V-ATPase, strain 74A of *N. crassa* was used. The strain was maintained on Vogel's medium N (a minimal medium salt solution at pH 5.8) supplemented with 2% sucrose. For membrane isolations, cells were grown approximately 14 hours at 25° C. in 4 liters of Vogel's medium inoculated with 10$^6$ conidia/ml (asexual spores) and aerated vigorously.

Chromaffin granule membranes were prepared from bovine adrenal glands, obtained fresh from a local abattoir, as described by Nelson et al., *Methods Enzymol.*, 157, 619-633 (1988). The membranes were stored in aliquots at −70° C. Vacuolar membranes were prepared from *N. crassa* as described by Bowman et al., *Biomembranes* (Packer, L., and Fleischer, S., eds), pp. 861-872, Academic Press San Diego (1997), and modified Bowman et al., *J. Biol. Chem.*, 272, 14776-14786 (1997).

Protein and ATPase activities were assayed as described by Bowman et al., *J. Biol. Chem.*, 272, 14776-14786 (1997), except that assays were done at 37° C. Poecillastrin A was added to assay mixtures from 5 or 10 mM stock solutions in dimethyl sulfoxide. When comparing the effects of the inhibitor on different membranes, the reactions were run at the same time in the same assay mix. Vacuolar-type (H+)-ATPase activities were measured at 37° C. with 2 µg of vacuolar membrane protein and various concentrations of poecillastrin A. Specific activities in the absence of inhibitor were 0.18 µmol/min/mg of protein for the Bovine CGM V-ATPase, and 5.0 mmol/min/mg of protein for the Nc VM V-ATPase. Each value was based on the average of three independent titrations. The results of the assay are shown in Table 4.

TABLE 4

| Compound | K$_i$ for Bovine CGM V-ATPase (µM) | K$_i$ for Nc VM V-ATPase (µM) |
|---|---|---|
| Poecillastrin A | 8.0 | 0.40 |

The foregoing data demonstrate that poecillastrin A is an effective inhibitor of vacuolar-type (H+)-ATPase, exhibiting K$_i$ values in the micromolar to sub-micromolar range.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of inhibiting vacuolar-type (H+)-ATPase in a patient in need thereof, the method comprising administering to the patient a vacuolar-type (H+)-ATPase-inhibiting effective amount of at least one compound of the formula:

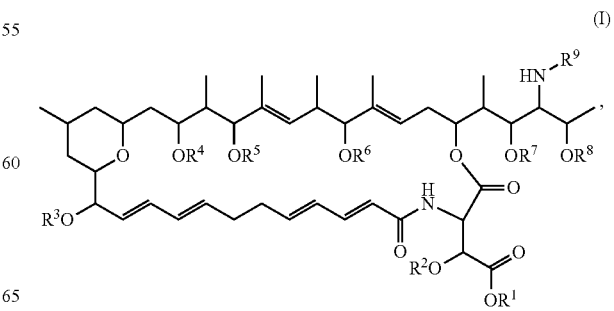

(I)

wherein:
R$^1$ is H, a straight-chain or branched C$_{1-30}$ saturated alkyl, a straight-chain or branched C$_{2-30}$ unsaturated alkyl, or an aryl comprising 6-10 carbon atoms in the ring skeleton thereof, wherein R$^1$ is unsubstituted or substituted with one or more substituents, which are the same or different, selected from the group consisting of a halogen, an oxo, OR$^{1a}$, CO$_2$R$^{1a}$, and OC(O)R$^{1a}$, wherein R$^{1a}$ is H, a straight-chain or branched C$_{1-30}$ saturated alkyl, a straight-chain or branched C$_{2-30}$ unsaturated alkyl, or an aryl comprising 6-10 carbon atoms in the ring skeleton thereof;
R$^2$-R$^8$ are the same or different and each is R$^{10}$, C(O)R$^{10}$, SO$_3$R$^{10}$, or SO$_2$R$^{10}$, wherein R$^{10}$ is H, a straight-chain or branched C$_{1-30}$ saturated alkyl, a straight-chain or branched C$_{2-30}$ unsaturated alkyl, or an aryl comprising 6-10 carbon atoms in the ring skeleton thereof, wherein R$^{10}$ is unsubstituted or substituted with one or more substituents, which are the same or different, selected from the group consisting of a halogen, an oxo, OR$^{10a}$, CO$_2$R$^{10a}$ and OC(O)R$^{10a}$, wherein R$^{10a}$ is H, a straight-chain or branched C$_{1-30}$ saturated alkyl, a straight-chain or branched C$_{2-30}$ unsaturated alkyl, or an aryl comprising 6-10 carbon atoms in the ring skeleton thereof; and
R$^9$ is a substituent of the formula:

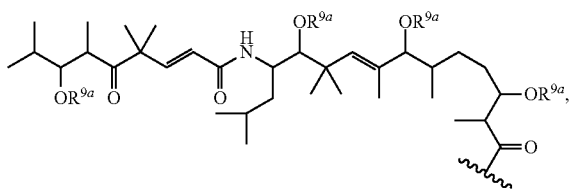

wherein the R$^{9a}$ substituents are the same or different and each is R$^{11}$, C(O)R$^{11}$, or SO$_2$R$^{11}$, wherein R$^{11}$ is H, a straight-chain or branched C$_{1-30}$ saturated alkyl, a straight-chain or branched C$_{2-30}$ unsaturated alkyl, or an aryl comprising 6-10 carbon atoms in the ring skeleton thereof, wherein R$^{11}$ is unsubstituted or substituted with one or more substituents, which are the same or different, selected from the group consisting of a halogen, an oxo, OR$^{11a}$, CO$_2$R$^{11a}$ and OC(O)R$^{11a}$, wherein R$^{11a}$ is H, a straight-chain or branched C$_{1-30}$ saturated alkyl, a straight-chain or branched C$_{2-30}$ unsaturated alkyl, or an aryl comprising 6-10 carbon atoms in the ring skeleton thereof;
wherein R$^{1a}$, R$^{10a}$ and R$^{11a}$ are unsubstituted or substituted with one or more substituents selected from the group consisting of a halogen, an oxo, and a hydroxyl; or a pharmaceutically acceptable salt thereof,
whereupon vacuolar-type (H+)-ATPase in the patient is inhibited.

2. The method of claim 1, wherein:
R$^1$ is H or a straight-chain or branched C$_{1-30}$ saturated alkyl;
R$^2$-R$^8$ are the same or different and each is R$^{10}$, wherein R$^{10}$ is H or a straight-chain or branched C$_{1-30}$ saturated alkyl; and
the R$^{9a}$ substituents are the same or different and each is R$^{11}$, wherein R$^{11}$ is H or a straight-chain or branched C$_{1-30}$ saturated alkyl;
or a pharmaceutically acceptable salt thereof,
whereupon vacuolar-type (H+)-ATPase in the patient is inhibited.

3. The method of claim 2, wherein:
R$^1$ is H or a straight-chain or branched C$_{1-6}$ saturated alkyl;
R$^2$-R$^8$ are the same or different and each is R$^{10}$, wherein R$^{10}$ is H or a straight-chain or branched C$_{1-6}$ saturated alkyl; and
the R$^{9a}$ substituents are the same or different and each is R$^{11}$, wherein R$^{11}$ is H or a straight-chain or branched C$_{1-6}$ saturated alkyl;
or a pharmaceutically acceptable salt thereof,
whereupon vacuolar-type (H+)-ATPase in the patient is inhibited.

4. The method of claim 1, wherein:
the compound is a compound of the formula:

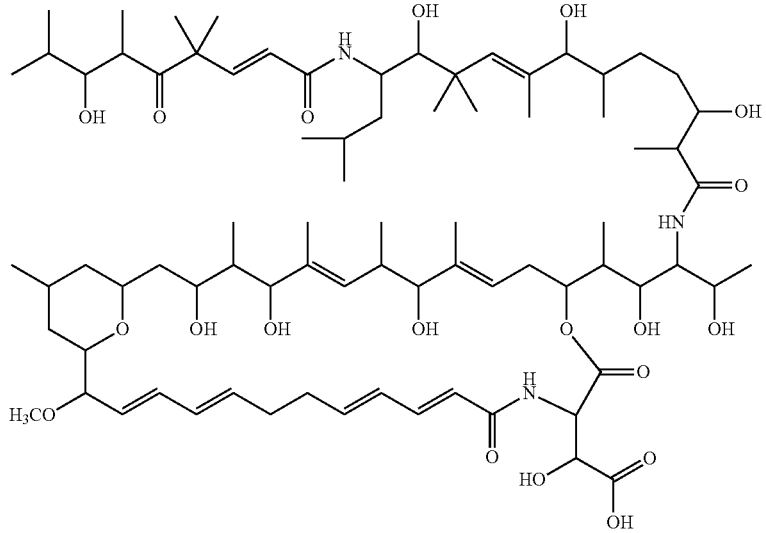

or a pharmaceutically acceptable salt thereof,
whereupon vacuolar-type (H+)-ATPase in the patient is inhibited.

5. The method of claim 4, wherein:
the compound is a compound of the formula:

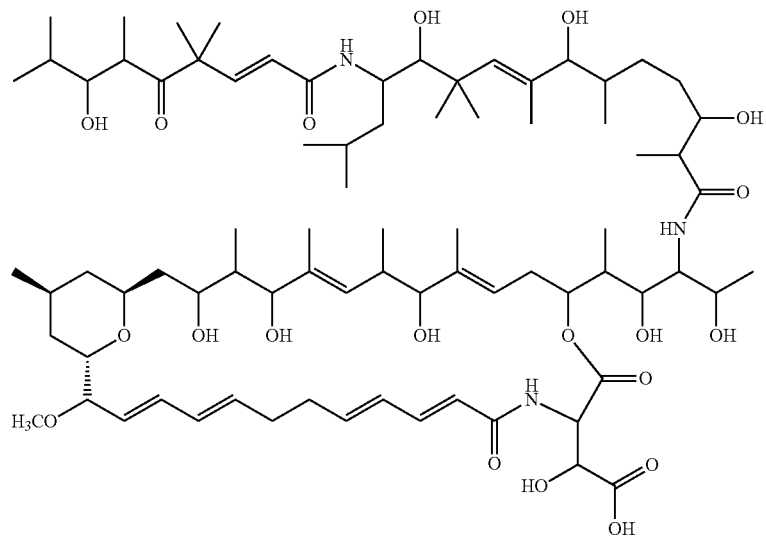

or a pharmaceutically acceptable salt thereof,
whereupon vacuolar-type (H+)-ATPase in the patient is inhibited.

6. The method of claim 1, wherein the patient is affected by a condition treatable by inhibition of vacuolar-type (H+)-ATPase.

7. The method of claim 6, wherein the condition is selected from the group consisting of osteoporosis, Alzheimer's disease, glaucoma, fertility, abnormal urinary acidification, abnormal secretion of degradative enzymes, fungal infection and cancer.

8. The method of claim 6, wherein the vacuolar-type (H+)-ATPase inhibiting-effective amount is effective to inhibit one or more conditions selected from the group consisting of intra-organellar acidification of intracellular organelles, urinary acidification, bone resorption, fertility, drug-resistance of tumor cells, tumor cell proliferation, cellular invasiveness, angiogenesis, and metastasis.

9. The method of claim 6, wherein the method further comprises administering a vacuolar-type (H+)-ATPase inhibiting-effective amount of at least one additional compound other than a compound of formula (I), which inhibits vacuolar-type (H+)-ATPase, wherein the at least one additional compound is salicylihalamide.

* * * * *